US006060503A

United States Patent [19]
Labrie et al.

[11] Patent Number: 6,060,503
[45] Date of Patent: May 9, 2000

[54] BENZOPYRAN-CONTAINING COMPOUNDS AND METHOD FOR THEIR USE

[75] Inventors: Fernand Labrie; Yves Merand; Sylvain Gauthier, all of Quebec, Canada

[73] Assignee: Endorecherche, Inc., Quebec, Canada

[21] Appl. No.: 08/388,207

[22] Filed: Feb. 21, 1995

Related U.S. Application Data

[60] Continuation-in-part of application No. 08/285,354, Aug. 3, 1994, Pat. No. 5,840,735, which is a division of application No. 07/801,704, Dec. 2, 1991, Pat. No. 5,395,842.

[51] Int. Cl.[7] .......................... A61K 31/40; A61K 31/44
[52] U.S. Cl. .......................... 514/428; 514/320; 514/337; 514/345
[58] Field of Search .................................. 514/337, 320, 514/277, 212, 425, 456, 345, 457, 428

[56] References Cited

U.S. PATENT DOCUMENTS

| | | | |
|---|---|---|---|
| 2,875,199 | 2/1959 | Cella | 260/239.57 |
| 3,321,483 | 5/1967 | Crenshaw | 260/293.4 |
| 3,396,169 | 8/1968 | Lednicer | 260/293.4 |
| 3,471,520 | 10/1969 | Irmscher et al. | 260/345.2 |
| 3,597,431 | 8/1971 | Coppola et al. | 260/288 |
| 3,995,060 | 11/1976 | Neri et al. | 424/324 |
| 4,094,994 | 6/1979 | Schonenberger et al. | 42/341 |
| 4,161,540 | 7/1979 | Neri et al. | 424/324 |
| 4,213,978 | 7/1980 | Bodor et al. | 424/241 |
| 4,368,080 | 5/1983 | Crossley et al. | 424/209 |
| 4,472,382 | 9/1984 | Labrie et al. | 424/177 |
| 4,659,516 | 4/1987 | Bowler et al. | 514/510 |
| 4,659,695 | 4/1987 | Labrie | 514/12 |
| 4,732,912 | 3/1988 | Pilgrim et al. | 514/510 |
| 4,751,240 | 6/1988 | Bowler et al. | 514/510 |
| 4,760,061 | 7/1988 | Edwards et al. | 514/211 |
| 4,904,661 | 2/1990 | Pilgrim et al. | 514/510 |
| 4,950,684 | 8/1990 | Koszyk et al. | 514/456 |
| 4,963,568 | 10/1990 | Schoenleber et al. | 514/320 |
| 4,975,455 | 12/1990 | Brion et al. | 514/456 |
| 5,021,432 | 6/1991 | Yamanaka et al. | 514/337 |
| 5,098,903 | 3/1992 | Magarian et al. | 514/255 |
| 5,204,337 | 4/1993 | Labrie et al. | 514/182 |
| 5,407,947 | 4/1995 | Bryant et al. | 514/320 |

FOREIGN PATENT DOCUMENTS

| | | |
|---|---|---|
| 124369 | 4/1984 | European Pat. Off. . |
| 153416 | 8/1984 | European Pat. Off. . |
| 0138504 | 10/1984 | European Pat. Off. . |
| 160508 | 4/1985 | European Pat. Off. . |
| 166509 | 4/1985 | European Pat. Off. . |
| 280618 | 2/1988 | European Pat. Off. . |
| 305242 | 7/1988 | European Pat. Off. . |
| 470310 | 8/1990 | European Pat. Off. . |
| 0652006 | 5/1995 | European Pat. Off. . |
| 2528434 | 6/1982 | France . |
| 2948733 | 12/1979 | Germany . |
| 3821148 | 6/1988 | Germany . |
| 8601105 | 8/1985 | WIPO . |
| 9010462 | 3/1990 | WIPO . |
| 9117749 | 5/1991 | WIPO . |
| 9221669 | 5/1992 | WIPO . |
| 9310741 | 6/1993 | WIPO . |

OTHER PUBLICATIONS

Asselin, et al., *J. Steroid Biochem.* 9:1079–1081 (1978).
Auchus, et al., *Biochemistry* 25:7295–7300 (1986).
Bhatnagar, et al., *J. Biol. Chem.* 253:811–815 (1978).
Blickenstaff, et al., *Steroids* 46:889–902 (1985).
Bucourt, et al., *J. Biol. Chem.* 253:8221–8228 (1978).
Bundgaard, *Textbook of Drug Design and Development*, pp. 113–191 (1991).
CA:107—No. 154111(b):678, Oct. 1987—Alberola, et al.
CA:113(23)—No. 211775W:744, Dec. 1990—Sharma, et al.
CA:117(9)—No. 90146p:90147, Sep. 1992—Kapil, et al.
CA:86(1)—No. 5271Z:5280, Jan. 1977—Badran, et al.
Chin, et al., *J. Biol. Chem.* 255:3660–3664 (1980).
Chin, et al., *J. Biol. Chem.* 250:7682–7686 (1975).
Crenshaw, et al., *J. Med. Chem.* 14(2):1185–1190 (1971).
Dhar, et al., *Contraception* 44(4):461–472 (1991).
Druzgala, et al., *J. Steroid Biochem. Mol. Bio.* 38:149–54 (1991).
Durani, et al., *J. Med. Chem.* 32:1700–1707 (1989).
Friend, *Critical Reviews in Therapeutic Drug Carrier Systems*, 7(2):149–186 (1990).
Furr, et al., *J. Endocr.* 113:R7–R9 (1987).
Jones, et al., *J. Med. Chem.* 22(8):962–966 (1979).
Jordan, et al., *Endocrinology* 124:1717–1726 (1989).
Klijn, et al., *J. Steroid Biochem.* 420(6B):1381 (1984).
Mouridsen, et al., *Cancer Treatment Rev.* 5:131–141 (1978).
Poulin, et al., *Cancer Res.* 46:4933–4937 (1986).
Pruitt, et al., *Organic Prep. & Proc. Int'l* 22(2):235–244 (1990).
Saeed, et al., *J. Med. Chem.* 33:3210–3216 (1990).
Sharma, et al., *J. Med. Chem.* 33:3216–3229 (1990).
Sharma, et al., *J. Med. Chem.* 33(12):3222–3229 (1990).
Simard, et al., *Mol Cell. Endo.* 39:141–1444 (1985).
Simard, et al., *Endocrinology* 126:3223–3231 (1990).
Simard, et al., *Mol. Cell. Endo.* 2:775–784 (1988).
Stoessel, et al., *J. Steroid Biochem.* 25(5A):677–682 (1986).
Thomas, et al., *J. Biol. Chem.* 258:1587–1590 (1983).
Thomas, et al., *J. Biol. Chem.* 258:11500–11508 (1983).
Tobias, et al., *J. Biol. Chem.* 257:2783–2786 (1982).
von Angerer, et al., *J. Med. Chem.* 27:1439–1447 (1984).
Von Angerer, et al., *J. Med. Chem.* 33:2635–2640 (1990).
Wakeling, et al., *J. Steroid Biochem.* 30:141–147 (1988).
Wakeling, et al., *Cancer Res.* 51:3867–3873 (1991).
Wakeling, et al., *J. Endo.* 112:R7–R10 (1987).

*Primary Examiner*—Theodore J. Criares
*Attorney, Agent, or Firm*—Ostrolenk, Faber, Gerb & Soffen, LLP

[57] ABSTRACT

Certain benzopyran antiestrogens are disclosed for treating estrogen sensitive diseases such as breast cancer. Prodrug forms provide ease of manufacturing, good shelf life, and bioavailability, and preferred stereoisomers are shown to be more effective than racemic mixtures.

84 Claims, 5 Drawing Sheets

BENZOPYRAN-CONTAINING COMPOUNDS AND METHOD FOR THEIR USE

RELATED APPLICATIONS

This application is a continuation-in-part of U.S. patent application Ser. No. 08/285,354 filed Aug. 3, 1994, now U.S. Pat. No. 5,840,735 which is in turn a divisional application of U.S. application Ser. No. 07/801,704 filed Dec. 2, 1991, now U.S. Pat. No. 5,395,842.

FIELD OF THE INVENTION

This invention relates to novel inhibitors of sex steroid activity such as antiestrogen compounds having effective antagonistic capability while substantially lacking agonistic effects. More particularly, certain preferred embodiments of the invention relate to certain substituted benzopyran compounds, especially certain prodrug species and certain stereospecific species, and to their use in the treatment of estrogen sensitive diseases.

BACKGROUND OF THE INVENTION

During the treatment of certain sex steroid-dependent diseases, it is important to greatly reduce or, if possible, eliminate certain sex steroid-induced effects. For this purpose, it is desirable both to block receptor sites stimulated by sex steroids and also to reduce the amount of sex steroid available to act at these sites. For example, alternative or concurrent therapy to administration of antiestrogens could involve attempts to block the production of estrogens (e.g. by ovariectomy) such that less is available to activate receptor sites. However, prior art methods for blocking estrogen production insufficiently inhibit estrogen-induced functions. Indeed, it is possible that even in the total absence of sex steroid, some receptors may be activated. See Simard and Labrie, "Keoxifene shows pure antiestrogenic activity in pituitary gonadotrophs", Mol. Cell. Endocrinol. 39: 141–144, (1985), especially page 144.

Hence, antagonists of sex steroids may produce greater therapeutic results than therapy which only inhibits sex steroid production. Prior art antagonists, however, often have insufficient affinity for receptors, and some, although capable of binding the receptors, may themselves act as agonists and undesirably activate the very receptors they are intended to shield from activation. There is, therefore, a need in the art for antiestrogens which effectively block estrogen receptors with minimal or no agonistic effect. The net effectiveness of a compound is affected by both its agonistic (undesirable) and antagonistic (desirable) activities. In Wakeling and Bowler, "Steroidal Pure Antioestrogens", J. Endocrinol. 112: R7–R10 (1987), certain steroid derivatives are said to act as an antiestrogens.

In U.S. Pat. No. 4,094,994, it is disclosed that the use of certain antiestrogens may inhibit certain human breast tumor cells.

H. Mouridsen et al., Cancer Treatm. Rev. 5: 131–141 (1978), discloses that Tamoxifen, an antiestrogen, is effective in remission of advanced breast cancer in about 30 percent of the women patients treated.

The combined use of the antiestrogen Tamoxifen and a luteinizing hormone-releasing hormone agonist, Buserelin, is also known for treatment of breast cancer. See, for instance, Klijn et al. J. Steroid Biochem. 420: no. 6B, 1381 (1984). The objective remission of such cancers, however, remains unacceptably low.

It has been found that certain 7αa-substituted derivatives of estradiol, for example a 7α—$(CH_2)_{10}$CONMeBu substitution, possess antiestrogenic activity (Bowler et al., 1985; Eur. Patent Application 0138504; Wakeling and Bowler, J. Steroid Biochem. 30: 141–147 (1988). See also U.S. Pat. No. 4,659,516. The substitution $(CH_2)_9SOC_5H_6F_5$ has also been used (Wakeling et al., Cancer Res. 51: 3867–3873, 1991).

Certain —$(CH_2)_{10}$CONMeBu substituted compounds are also disclosed in U.S. Pat. No. 4,732,912 (See e.g. example 5 and 16). See also EP Pat. No. 166 509, EP Pat No. 124 369, EP Pat. No. 160 508, EP Pat. No. 163 416, U.S. Pat. No. 4,760,061, U.S. Pat. No. 4,751,240 and Wakeling A. E. and Bowler, J., J. Endocrinol. 112: R7–R10 (1987).

Von Angerer et al. discuss other antiestrogens in "1-(aminoalkyl)-2-phenylindoles as Novel Pure Estrogen Antagonists", J. Med. Chem. 1990; 33: 2635–2640. In U.S. Pat. No. 4,094,994, where it is said that the use of certain antiestrogens inhibit certain human breast tumor cells. See also DE 3821148.

A. Saeed et al., J. Med. Chem. 33: 3210–3216, 1990; A. P. Sharma et al., J. Med. Chem. 33: 3216–3222 and 3222–3229 (1990) described the synthesis and biological activities of certain 2,3-diaryl-2H-1-benzopyran analogs having the following molecular structure:

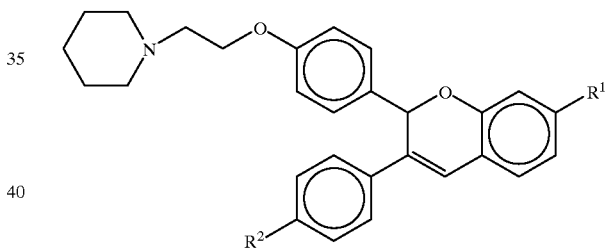

for use as antiestrogens. In N. Durani et al., J. Med. Chem. 32: 1700–1707 (1989), the synthesis and biological activities of benzofuran and triarylfuran analogues as antiestrogens are described.

In applicant's grandparent priority application hereto, an international version of which is now published as WO 93/10741, a class of improved estrogen activity inhibitors is disclosed, including the inhibitor EM-343, i.e. 7-hydroxy-3-(4'-hydroxyphenyl)-4-methyl-2-(4"-(2'"-piperidinoethoxy)phenyl-2H-benzopyran and its prodrugs. The present invention relates in part to particular types of benzopyran antiestrogens and to certain modified benzopyran antiestrogens, all of which provide further improved characteristics. It has now been found that certain prodrugs of EM-343 provide advantages that are especially efficacious. EM-343 may exert as either of two enantiomers or as a mixture of the two. It has now been discovered that one of the two enantiomers is more effective than the other. That more effective enantiomer and prodrugs thereof are also the subject of the present invention.

Derivatives of active drugs which are, by in vivo enzymatic or spontaneous reactions, transformed into the active drugs are known (see H. Bundgaard, Design and Application of Prodrugs. In A textbook of Drug Design and Development; Edited by P. Krogsgaard-Larsen and H. Bundgaard; Harwood Academic Publishers GmfH, Chur, Switzerland, 1991, pp. 113–191). In the steroid series, for example, Druzgala et al. (J. Steroid Biochem. Molec. Biol. 38, 149–154, 1991) have described prodrugs of glucocorticoids. Bodor et al. in U.S. patent application No. 4,213,978 and in German Patent Application Publication No DE 29 48 733 disclose the use of thiazolidine derivatives of progesterone as topical drugs. Percutaneous absorption of prodrug derivatives of estrogens and progestins are reported by Friend DR in Critical Reviews in Therapeutic Drug Carrier Systems, vol. 7 (2), pp. 149–186, 1990.

OBJECTS OF THE INVENTION

It is an object of the invention to provide compounds and compositions for reducing estrogen receptor activation, including certain prodrugs and optically active species.

It is another object to provide a non-steroidal antiestrogen having good affinity for estrogen receptors, but substantially lacking undesirable agonistic activity regarding these receptors and substantially lacking hormonal activity.

It is another object of the invention to provide therapeutic compounds and compositions useful in the treatment of estrogen-related diseases (e.g. diseases whose onset or progress is aided by activation of the estrogen receptor). These diseases include, but are not limited to breast cancer, uterine cancer, ovarian cancer, endometriosis, uterine fibroma, precocious puberty and benign prostatic hyperplasia.

It is another object to provide prodrugs that are easy to synthesize and purify, that have good bioavailability, and that have good shelf stability while easily undergoing conversion to a desired active ingredient in vivo.

SUMMARY OF THE INVENTION

The above and other objects are provided by the compounds discussed herein, by pharmaceutical compositions thereof, and by utilizing the compounds of the invention (or pharmaceutical compositions containing them) in the treatment of sex steroid dependent diseases. For example, breast cancer, endometrial cancer and other estrogen-dependent diseases, whose onset or progress is facilitated by estrogen activity, are believed to respond favorably to treatment with the compounds and compositions of the invention.

In one embodiment, the invention provides a compound or pharmaceutically acceptable salt thereof, said compound having the molecular structure:

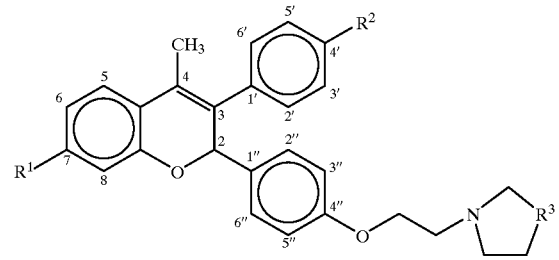

wherein $R^1$ and $R^2$ are independently selected from the group consisting of hydroxyl and a moiety convertable in vivo to hydroxyl;

wherein $R^3$ is —$CH_2$— or —$CH_2CH_2$—; and wherein said compound or salt includes more than 50% (by weight relative to all stereoisomers) of stereoisomers that have an absolute configuration at their chiral number 2 carbon identical to EM-652's, absolute configuration at EM-652's chiral number 2 carbon.

Preferred compounds have the same absolute configuration at their number 2 carbon as EM 652 ((+)-7-hydroxy-3-(4'-hydroxyphenyl)-4-methyl-2-(4"-(2'"-piperidinoethoxy)phenyl)-2H-benzopyran) has at its number 2 carbon.

.In another embodiment, the invention provides a compound or pharmaceutically acceptable further salt thereof, said compound having the molecular structure:

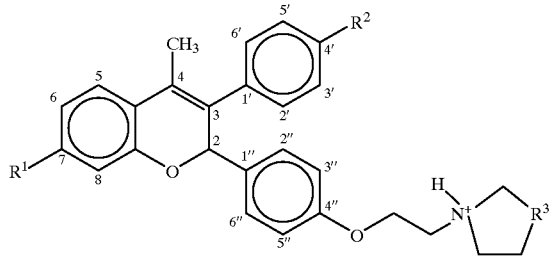

wherein $A^-$ is an anion of a pharmaceutically acceptable acid;

wherein $R^1$ and $R^2$ are independently selected from the group consisting of hydroxyl and a moiety convertable in vivo to hydroxyl; and wherein $R^3$ is —$C_2$— or —$CH_2CH_2$—.

In another embodiment, the invention provides a compound or pharmaceutically acceptable salt thereof, said inhibitor having the molecular structure:

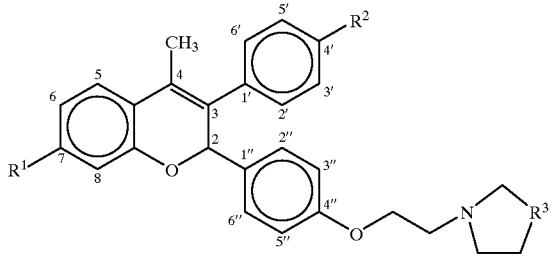

wherein $R^3$ is —$CH_2$— or —$CH_2CH_2$—; and wherein at least one of $R^1$ or $R^2$ is a moiety convertable in vivo to hydroxyl.

In an other embodiment, the invention provides an optically active compound of the following molecular structure:

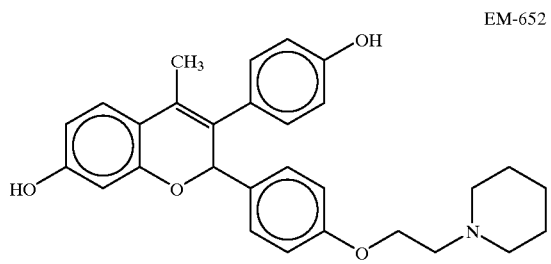

or a pharmaceutically acceptable salt thereof.

In an other embodiment, the invention provides an optically active compound of the following molecular structure:

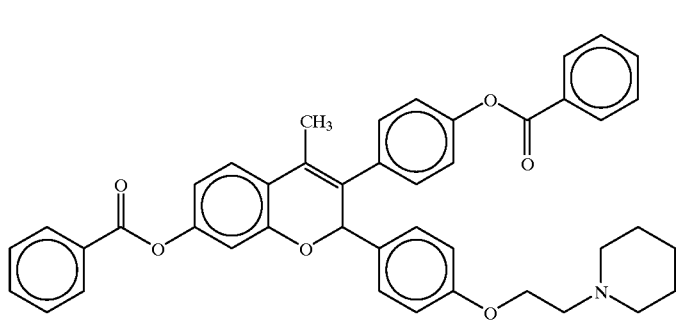

or a pharmaceutically acceptable salt thereof.

In an other embodiment, the invention provides an optically active compound of the following molecular structure:

or a pharmaceutically acceptable salt thereof.

In an other embodiment, any of the compounds discussed herein are formulated together with a pharmaceutically acceptable diluent or carrier as pharmaceutical compositions containing the active compounds of the invention.

In an other embodiment, any of the compounds or pharmaceutical compositions of the invention are administered to patients as a method of treating breast cancer, endometrial cancer or other estrogen sensitive disease whose onset or progress is caused or enhanced by estrogen activity.

A "moiety converted in vivo into hydroxyl" is a moiety which is cleaved and replaced by a hydroxyl group or the corresponding anion by chemical or enzymatic processes of the body. Many such groups are known in the art (see e.q. Textbook of drug Basics and Development; (Edited by P. Krogrgaard-Garsen and H. Bundgaard), Harwood Academic Publishers, GmfH, Chur, Switzerland, 1991, especially p. 154). Non limiting examples of such groups are alkyloxy, alkenyloxy, aryloxy, alkylcarboxyl, alkoxycarboxyl, dialkylaminocarboxyl and silyloxy which (when positioned as shown in the compounds of the invention) are converted to hydroxyl.

Prodrugs of the racemic version of EM-343 ((±)-7-hydroxy-3-(4'-hydroxyphenyl)-4-methyl-2-(4"-(2'"-piperidinoethoxy)phenyl-2H-benzypyran) and especially the dextrorotatory enantiomeric species of EM-343 designated herein as "EM-652", ((+)-7-hydroxy-3-(4'-hydroxyphenyl)-4methyl-2-(4"-(2'"-piperidinoethoxy) phenyl-2H-benzypyran) are preferred, although the invention is not limited to these species.

The invention contemplates salts (including complex salts) and prodrug forms of compounds discussed herein.

Except where specificied to the contrary, the following conventions apply to molecular structures and formulae set forth herein. Substituents may have either R or S stere-

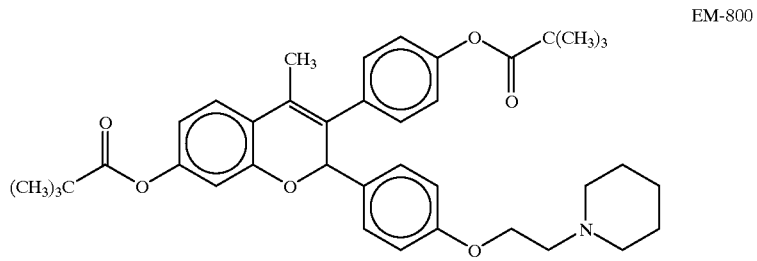

ochemistry. Any moiety of more than two atoms may be straight-or branched-chain unless otherwise specified.

The compounds discussed herein may exist either as racemic mixtures or optically active species except when otherwise specified. The term "antiestrogen", when used herein to describe the compounds of the invention, is not intended to imply that the compounds do not provide other beneficial functions besides antagonistic activity (e.g., inhibition of enzymes as discussed above), and the term also includes both biologically active compounds and prodrug forms thereof that are convertible in vivo to the biologically active species.

Without intending to be bound by theory, it is believed that the novel compounds and pharmaceutical compositions of the invention are useful in the treatment of estrogen-related diseases because of their ability to inhibit activation of the estrogen receptor. It is believed that active forms of the compounds of the invention reduce activation of estrogen receptors by a variety of mechanisms. One likely mechanism is an "antiestrogenic" function wherein the compounds of the invention bind estrogen receptors and block access to those receptors by estrogens. It is also believed that the compounds of the invention substantially lack inherent estrogenic activity. In other words, it is believed that the compounds of the invention have little, if any, inherent ability to activate estrogen receptors to which they bind, and are not easily converted in vivo to compounds having significant inherent estrogenic activity. Another mechanism by which many compounds of the invention may function is by inhibiting the action of enzymes which produce sex steroids or their precursors. Examples of such enzymes which may be inhibited by the compounds of the invention include but are not limited to aromatase, 17β-hydroxysteroid dehydrogenase, 3β-hydroxysteroid dehydrogenase and the like.

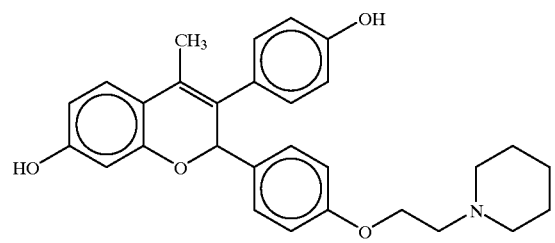

and its dextrogyric enantiomer EM-652 on estradiol-induced cell proliferation in ZR-75-1 human breast cancer cells. The respective $IC_{50}$ values are calculated at $2.4 \times 10^{-10}$M for EM-343 and $1.1 \times 10^{-10}$M for EM-652 thus indicating a 2-fold higher activity for EM-652. As used herein, the term "EM-343" (except where specifically described as a racemic mixture) includes any enantiomer having the molecular structure set forth above and includes mixtures thereof including the racemic mixture. The terms "EM-651" and "EM-652" are reserved for optically active versions of EM-343 enhanced in the concentration of the levorotatory or dextrorotatory enantiomer, respectively.

Figure 2:
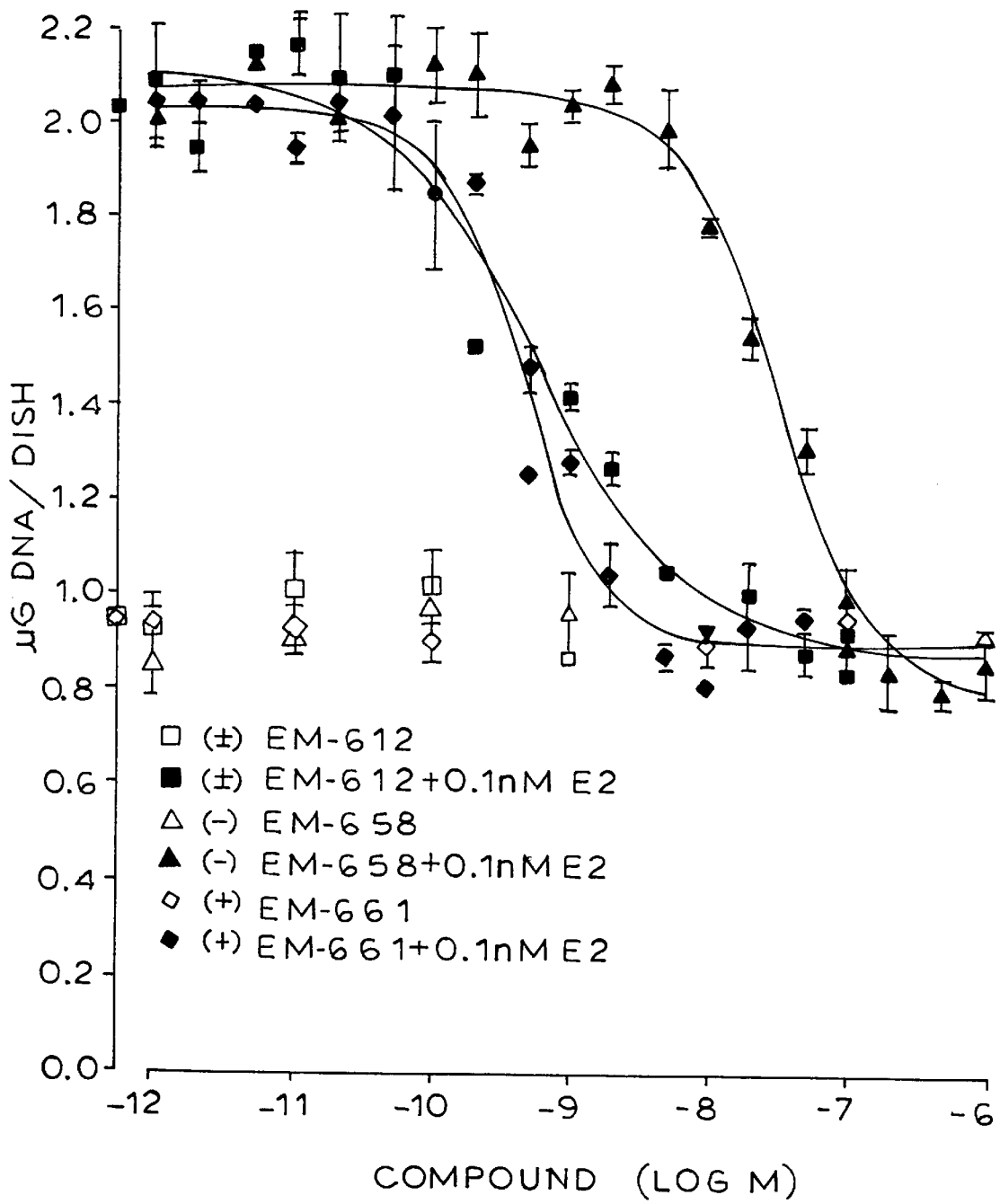

FIG. 2 illustrates the comparative inhibitory activity of increasing concentrations of a racemic version of EM-612, the dibenzoate of EM-343 having the following structure:

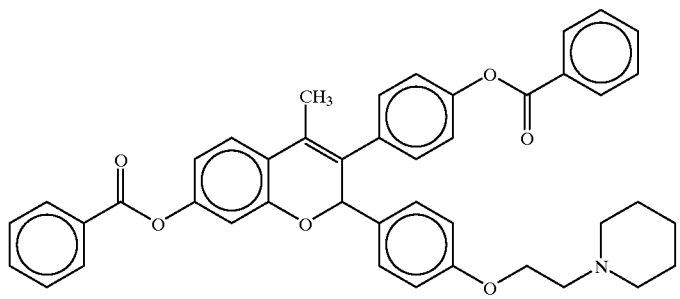

versus EM-661 (optically active and enriched in the dextrogyric enantiomer of EM-612), and EM-658 (optically active and enriched in the levogyric enantiomer of EM-612) on estradiol-induced cell proliferation in ZR-75–1 human breast cancer cells. The respective $IC_{50}$ values are calculated at $5.76 \times 10^{-10}$M for EM-612, $4.37 \times 10^{-10}$M for EM 661 and $3.01 \times 10^{-8}$M for EM-658, thus indicating a 69-fold higher activity for the dextrogyric enantiomer EM-661 compared to the levogyric enantiomer EM-658.

Figure 3:
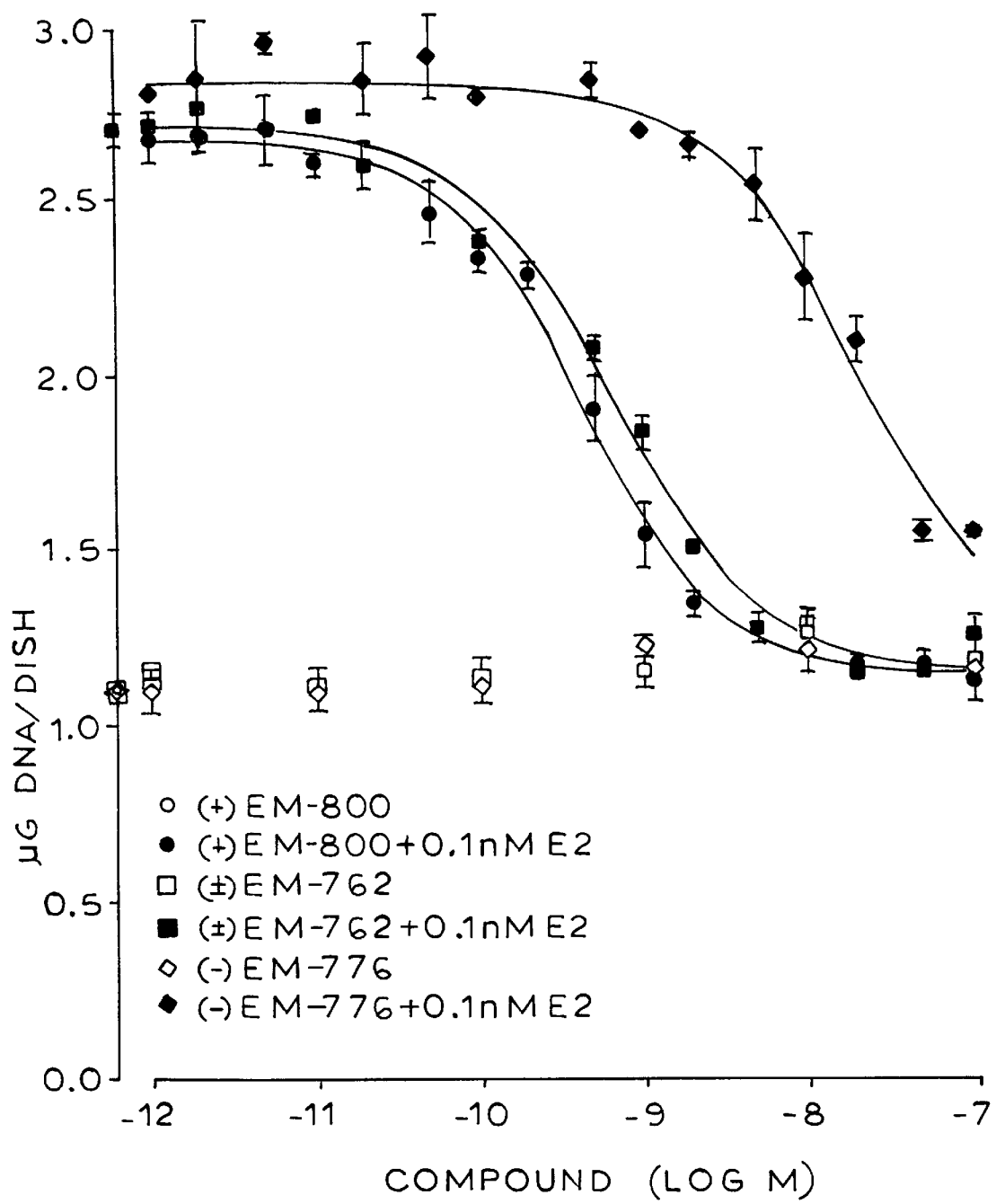

FIG. 3 illustrates the comparative inhibitory activity of increasing concentrations of the racemic version of EM-762, the dipivalate of EM-343 having the following structure:

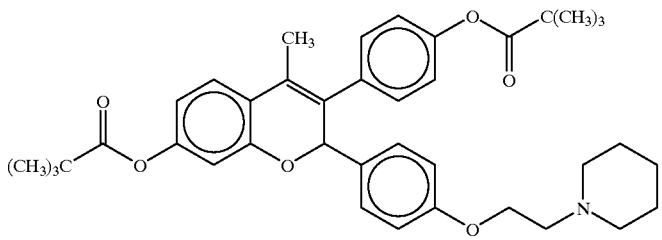

versus EM-800 (optically active and enriched the dextrogyric enantiomer of EM-762, and EM-776 (optically active and enriched in the levogyric enantiomer of EM-762) on estradiol-induced cell proliferation in ZR-75-1 human breast cancer cells. The respective $IC_{50}$ values are calculated at $6.47 \times 10^{-10}$M for EM-762, $4.37 \times 10^{-10}$M for EM-800, and $1.9 \times 10^{-8}$M for EM-776, thus indicating a 43-fold higher activity for the dextrogyric enantiomer EM-800 compared to the levogyric enantiomer EM-776.

Figure 4:
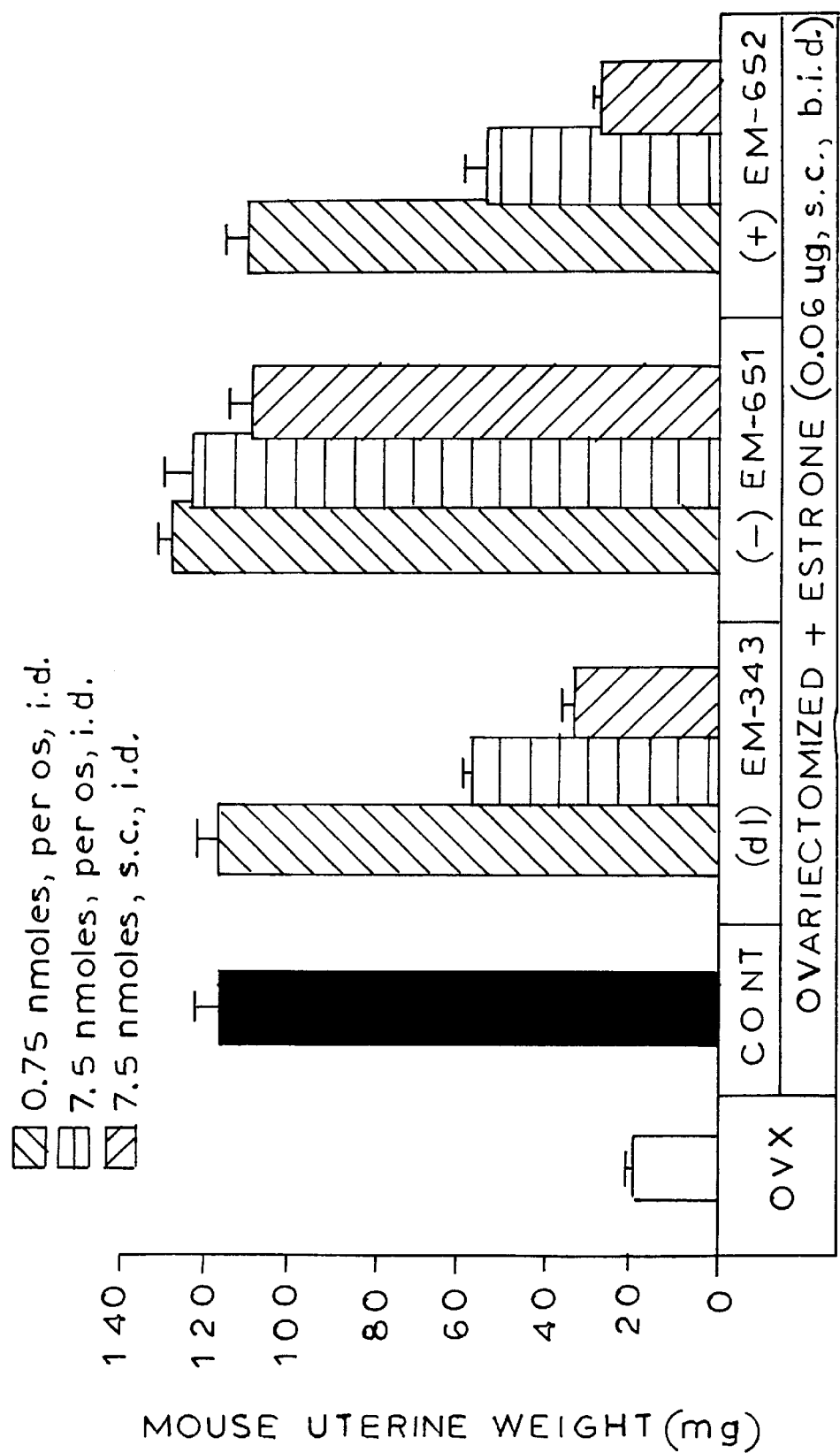

FIG. 4 likewise illustrates the effect of racemic EM-343 versus its levogyric enantiomer EM-651 and its dextrogyric enantiomer EM-652, administered once daily in the indicated manner and dosage, on uterine weight (mg) in adult female ovariectomized Balb/C mice treated for 9 days (from day 3 to the day 11 after ovariectomy) in the indicated presence or absence of simultaneous treatment with estrone (0.06 μg, s.c., twice daily, from day 6 to day 11 after ovariectomy). Estrone is a precursor of the potent estrogen estradiol. The data presented is therefore indicative of the compound's ability to block estrogen receptors (i.e., act as an antiestrogen), and perhaps is also indicative of the compound's ability to inhibit conversion of estrone to estradiol.

Figure 5:
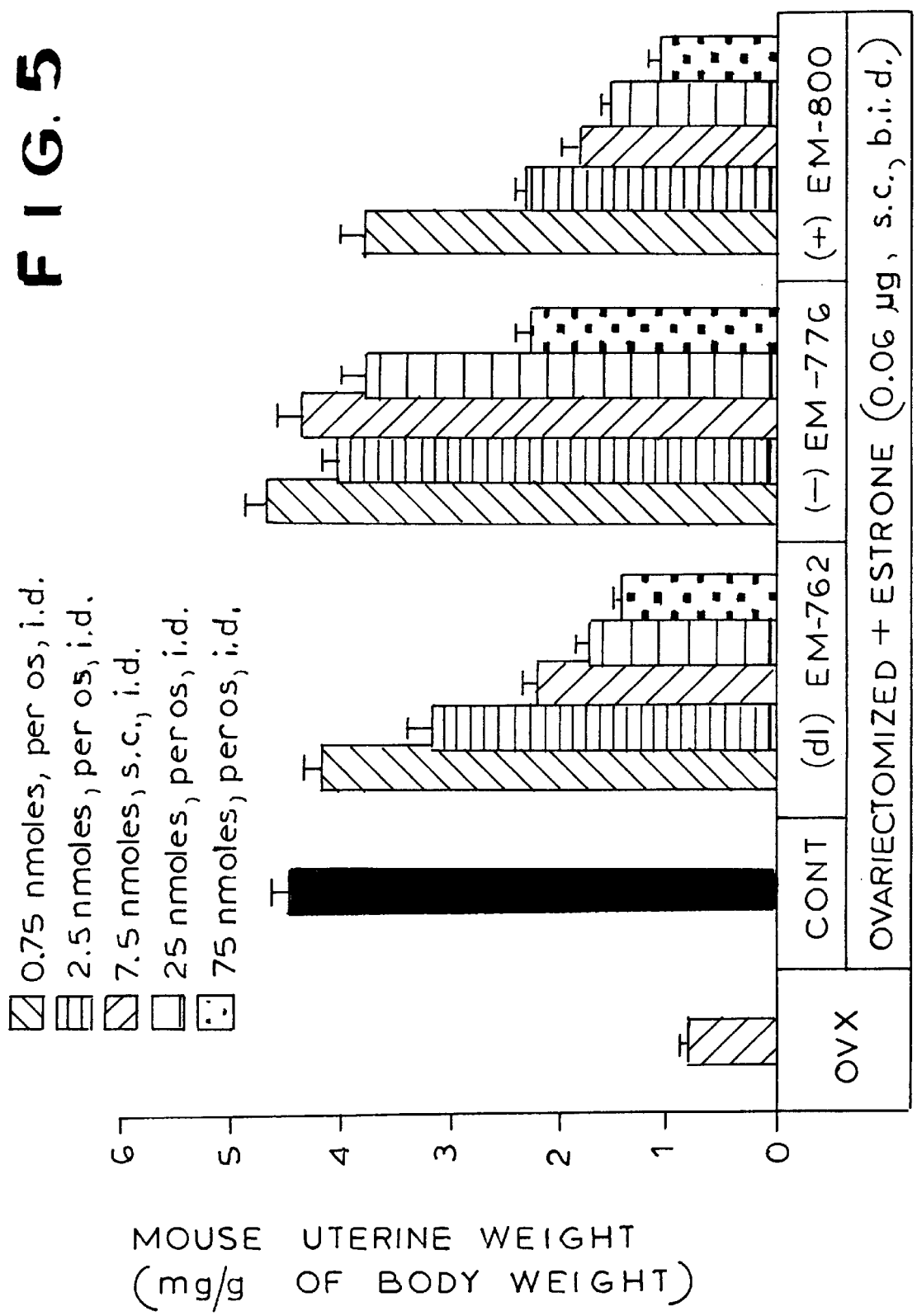

FIG. 5 illustrates the effect of the indicated doses of the racemic version of EM-762, a dipivalate of EM-343 having the following molecular structure:

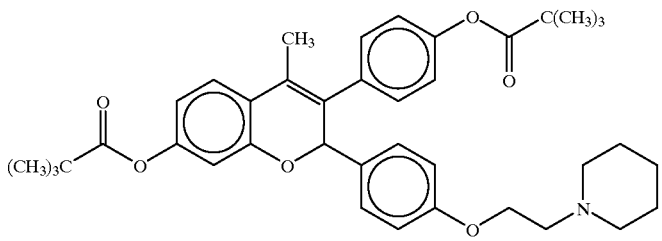

versus its levogyric enantiomer EM-776 and its dextrogyric enantiomer EM-800 orally administered once daily on uterine weight (mg) in adult female ovariectomized Balb/C mice treated for 9 days (from day 3 to day 11) after ovariectomy in the indicated presence or absence of simultaneous treatment with estrone (0.06 μg, s.c., twice daily, from day 6 to day 11 after ovariectomy).

The invention is further illustrated by the detailed description of preferred embodiments which are set forth below by way of illustration only. The invention is not limited to these preferred embodiments.

DETAILED DESCRIPTION OF THE PREFERRED EMBODIMENTS

Preferred prodrugs of the invention include those wherein at least one of the hydroxy substituents of the benzopyran phenyl groups of the active species (e.g., the hydroxyl groups of EM-343 or of its dextrorotatory enantiomer, EM-652) is replaced with a substituent that is converted in vivo to hydroxyl. Numerous such moieties convertible to hydroxyl in vivo are known in the art (see page 154 of Bundgaard, H., "Design and Application of Prodrugs," *A Textbook of Drug Design & Development*, Bundgaard & Krogsgaard-Larsen, Ed., (Harwook Academic Publishers GmfH, Chur, Switzerland), 1991. Prodrugs have now been developed by applicants which (1) have good crystallinity and are therefore easier to synthesize and purify; (2) have good shelf stability yet sufficiently unstable in vivo to desirably be converted to a preferred active compound; (3) good bioavailability (e.g. ability to pass through membranes or otherwise reach desired locations after administration); and (4) low toxicity of metabolites.

It has now been discovered by applicants that the prodrug forms which provide the best combination of good results under the foregoing parameters are prodrugs wherein one or more of the foregoing of the hydroxyl groups of the active compounds are replaced, in the prodrug form, by acyloxy groups, preferably aliphatic or aromatic acyloxy, and most preferably a hindered (e.g. branched or alicydlic) aliphatic acyloxy, especially pivaloyloxy. In other embodiments, a hydroxyl substituent of an active species may be replaced by inter alia a function selected from the group consisting of:

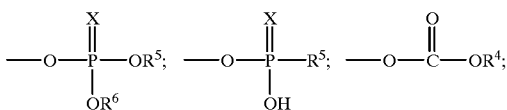

-continued

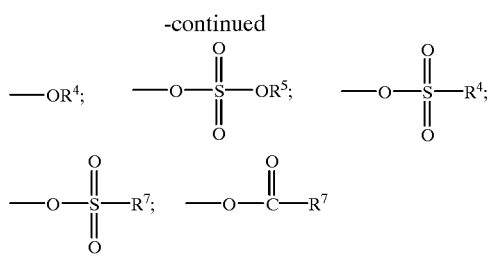

wherein X is sulfur or oxygen;
$R^4$ is selected from the group consisting of alkyl, alkenyl, alkynyl, and aryl;
$R^5$ and $R^6$ are independently selected from the group consisting of hydrogen, alkyl, alkenyl, alkynyl, aryl and a cation; and
$R^7$ is selected from the group consisting of amino, alkylamino, aminoalkyl, and alkylsulfanyl.

When the absolute configuration of molecular structures discussed herein is not specified, those molecular structures may include one or more stereoiomers resulting from any chiral centers present, may include racemic mixtures, or may be optically active. It has now been found by the inventors that certain enantiomers of the compounds of the invention are more effective than others in the treatment of estrogen-related diseases, and in desirably inhibiting estrogen receptor activation. The present invention contemplates improving effectiveness by selectively enhancing the concentration of the more potent enantiomers relative to the less potent enantiomers, and by thus providing optically active products for use in the treatment of estrogen-related diseases. In preferred embodiments, optically active antiestrogens of the invention comprise at least 90% of the more potent enantiomers, and are preferably substantially pure in that enantiomer.

All of the compounds discussed herein have a chiral center at their number two carbon. It has been found that the most potent stereoisomers among the antiestrogens of the invention are those that have the same absolute configuration at their chiral number two carbon as does EM-652, the dextrorotatory enantiomer of the following antiestrogen:

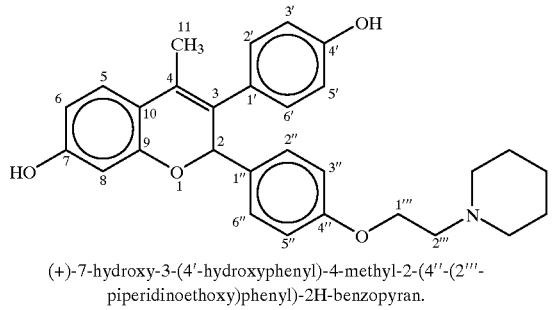

(+)-7-hydroxy-3-(4'-hydroxyphenyl)-4-methyl-2-(4''-(2'''-piperidinoethoxy)phenyl)-2H-benzopyran.

Preferred stereoisomers always have the same absolute configuration at their number two carbons as EM-652, but may not necessarily be dextrorotatory when a second chiral center appears somewhere else in their molecular structure. However, where there is only a single chiral center, the preferred enantiomer will be dextrorotary. Preferred prodrug forms that include a second chiral center in a part of the molecular structure that is removed in vivo still have the same preferred absolute configuration at carbon two as has EM-652. Thus, the active forms to which the prodrugs convert in vivo will not include the second chiral center and will be dextrorotatory (even in instances where the prodrug form, due to its temporary second chiral center, might be levorotatory). To verify that a particular optically active species is of the preferred absolute configuration, the species rotation of a plane of polarized light may be determined by techniques well known in the art. Where there are other chiral centers in a prodrug form of the invention, the prodrugs should first be converted to the active species by a mild technique known in the art not to racemize or invert the remaining chiral center of the active species (see e.g. Example 8), or otherwise freed of chiral centers other than carbon two, before measuring the rotation of polarized light by the resulting active compound. If that rotation indicates a dextrorotatory active compound (following removal of any second chiral center that may have existed on the prodrug form), then both the prodrug form and the resultant active form are in the preferred absolute configuration at carbon 2.

Compounds of the invention include a nitrogen hetero ring. In some but not all embodiments, salts are contemplated wherein the nitrogen of the hetero-ring is a charged quaternary nitrogen associated with a pharmaceutically acceptable acid anion. The invention also contemplates complex salts wherein the nitrogen of the hetero ring is not the only charged "salt" position in the overall molecular structure. Preferred embodiments are optically active and have EM-652's absolute configuration at carbon 2 (verifyable by extracting the salt under basic conditions, thus arriving at a free base with only one chiral center at carbon 2 whose absolute stereochemistry can then be verified by checking for the desired dextrorotatory optical activity).

When administered systemically, preferred uses of the pharmaceutical compositions and compounds of the invention include but are not limited to treatment of breast cancer, endometrial cancer, uterine cancer, ovarian cancer, endometriosis, uterine fibroma, precocious puberty and benign prostatic hyperplasia. Other estrogen-sensitive diseases whose onset or progress is aided by estrogen activity may respond favorably to treatment in accordance with the invention.

Especially during the early course of treatment, it is preferred to take occasional blood samples and to alter dosage as necessary to maintain serum concentration of the active compound of the invention or sum of the active compounds (where more than one is administered) between about 0.2 μg/ml and 10 μg/ml. The attending clinician may elect to alter this target concentration depending upon observed patient response.

Compounds administered in accordance with the invention are preferably administered in a dosage range between 0.01 to 10 mg/kg of body weight per day (preferably 0.05 to 1.0 mg/kg), with 5 mg per day, especially 10 mg per day, in two equally divided doses being preferred for a person of average body weight when orally administered, or in a dosage range between 0.003 to 3.0 mg/kg of body weight per day (preferably 0.015 to 0.3 mg/ml), with 1.5 mg per day, especially 3.0 mg per day, in two equally divided doses being preferred for a person of average body weight when parentally administered (i.e. intramuscular, subcutaneous or percutaneous administration). Preferably the compounds are administered together with a pharmaceutically acceptable diluent or carrier as described below.

Preferred pharmaceutical compositions comprise therapeutically effective amounts of at least one of the compounds discussed herein wherein a pharmaceutically acceptable diluent or carrier is included with the active compound (s). The concentration of the active compound (which term includes the prodrugs discussed herein) in said diluent or carrier will vary in accordance with known techniques depending upon the manner in which the pharmaceutical composition is to be administered.

A composition suitable for oral administration may preferably include at least one inhibitor of sex steroid activity described herein wherein the total concentration of all such inhibitors in said pharmaceutical composition is from about 0.2% to about 95% of the composition (by weight relative to the total), and preferably from about 1% to about 10%. A pharmaceutically acceptable diluent, for example, starch or lactose with or without tartrazine, is preferably included.

When prepared for parenteral injection, an inhibitor of sex steroid activity is preferably added at a concentration between about 0.5 mg/ml and about 100 mg/ml (preferably about 1 mg/ml to about 5 mg/ml) into a carrier preferably comprising at least one of saline, water, aqueous ethanol, aqueous dimethylsulfoxide, and oil.

A composition suitable for continuous parenteral administration preferably contains a carrier and an antiestrogen in accordance with the invention at a concentration sufficient to introduce from about 0.5 mg to about 500 (preferably 2.5 to 50) mg of the antiestrogen per 50 kg of body weight per day at the volume flow rate used. The volume flow should thus vary with the concentration to achieve the desired result. At higher concentrations, less volume flow is needed and at lower concentrations, more.

In certain alternative embodiments, the pharmaceutical composition of the invention may be formulated for sustained release in accordance with known techniques. These sustained release formulations are preferably prepared in an appropriate manner for either oral, intramuscular, or subcutaneous administration. The compounds may also be administered by transdermal patch in accordance with known techniques. These sustained release formulations, in accordance with the invention, must be formulated to introduce from about 0.5 to 500 mg (preferably 2.5 to 50 mg) of the antiestrogen per 50 kg of body weight per day.

Set forth below are some flow charts, descriptions and illustrations of a number of preferred synthesis schemes for certain preferred compounds in accordance with the invention. The steps set forth below are set forth merely by way of example. Those of skill in the art will readily recognize alternative synthetic pathways and variations capable of producing a variety of compounds full in accordance with the invention.

EXAMPLES OF SYNTHESES OF PREFERRED SEX STEROID ACTIVITY INHIBITORS

Instrumentation

The IR spectra herein were taken on a Perkin-Elmer 1600 Series FT-IR spectrophotometer. Proton NMR spectra were recorded on a Brucker AC-F 300 instrument. The following abbreviations have been used: s, singlet; d, doublet; dd, doublet of doublet; t, triplet; q, quadruplet, and m, multiplet. The chemical shifts ($\delta$) were referenced to chloroform (7.26 ppm for $^1$H and 77.00 ppm for $^{13}$C) and were expressed in ppm. Optical rotations were measured at room temperature on a Jasco DIP 360 polarimeter. Mass spectra (MS) were obtained on a V.G. Micromass 16F machine. Thin-layer chromatography (TLC) was performed on 0.25 mm Kieselgel 60F254 plates (E. Merck, Darmstadt, FRG). For flash chromatography, Merck-Kieselgel 60 (230–400 mesh A.S.T.M.) was used. Unless otherwise noted, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure.

| | LIST OF ABBREVIATIONS |
|---|---|
| DHP | 3,4-dihydro-2H-pyran |
| EDTA | Ethylenediaminetetraacetic acid |
| HPLC | High pressure liquid chromatography |
| PTSA | p-toluenesulfornic acid |
| THF | Tetrahydrofuran |
| THP | Tetrahydropyranyl |
| TMS | Tetramethylsilyl |

Example 1

Synthesis of 7-hydroxy-3-(4'-hydroxyphenyl)-4-methyl-2-(4''-(2'''-piperidinoethoxy)phenyl)-2H-benzopyran (EM-343)

SYNTHESIS A (This synthesis is described below in Scheme 1)

SCHEME 1

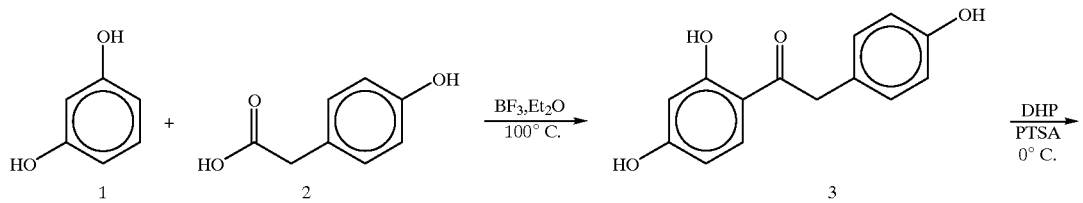

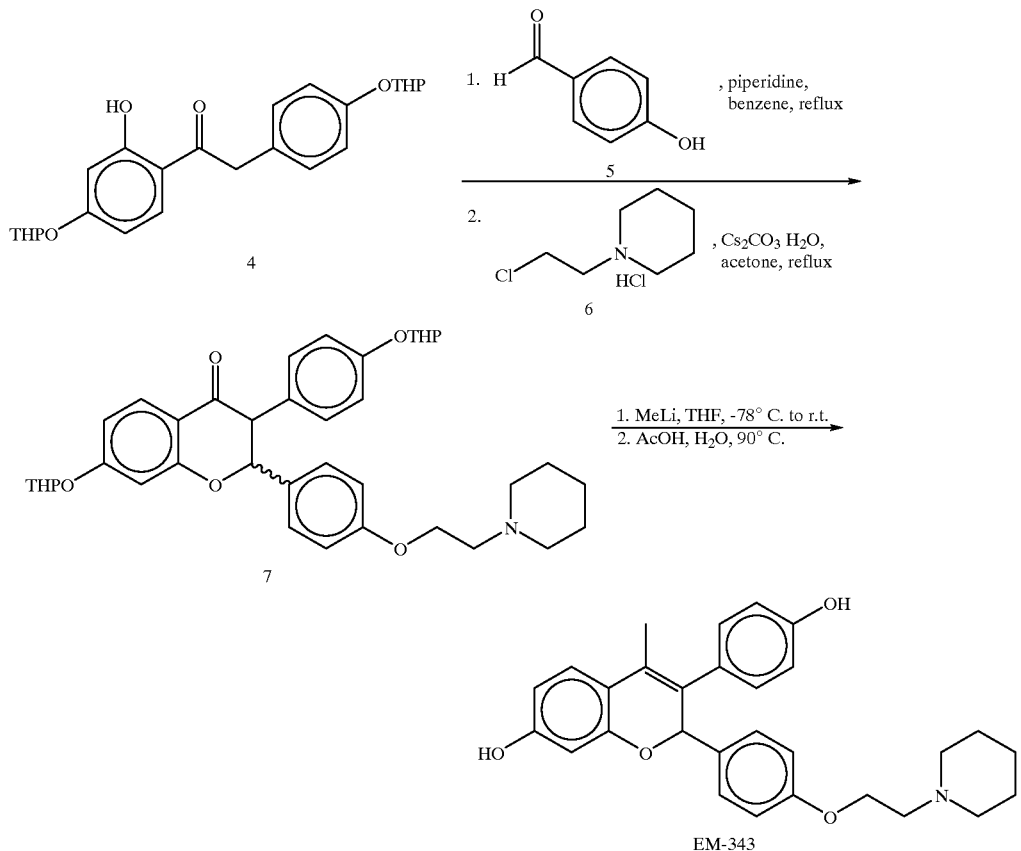

The foregoing synthesis was carried out as follows:

Triphenol 3

A suspension of resorcinol 1 (89.2 g, 0.810 mol) and acid 2 (135.4 g, 0.890 mol) (both compounds are available from Aldrich Chemical Company Inc., Milwaukee, Wis.) in boron trifluoride etherate (300 mL) and toluene (240 mL) was heated at 100° C. for 3 h and then allowed to cool to room temperature. The resulting suspension was stirred overnight with 12% aaueous sodium acetate (400 mL). The resulting precipitate was filtered, washed with distilled water (2×1 L) and 12% aqueous sodium acetate (400 mL). The solid was then stirred with 12% aqueous sodium acetate (1.2 L) overnight. The precipitate was filtered, washed with distilled water (500 mL) and recrystallized (ethanol:water; 0.75:3 L) to yield the triphenol 3 (160.2 g, 81%) which was dried for one week under vacuo (mp. 180–185° C.).

Ditetrahydropyranyl Ether 4

A suspension of triphenol 3 (164 g, 0.672 mol) in 3, 4dihydro-2H-pyran (600 mL) (available from Aldrich Chemical Company Inc., Milwaukee, Wis.) was treated with p-toluenesulfonic add monohydrate (2×10 mg) at 0° C. The reaction mixture was stirred for 1.5 h at 0° C. and then for 1 h after removing the ice bath (the reaction was monitored by TLC; p-toluenesulfonic acid monohydrate was added until starting material and monotetrahydropyranyl ether had disappeared). The mixture was then treated with saturated sodium bicarbonate (250 mL) and ethyl acetate (1 L). The organic phase was washed with saturated sodium bicarbonate (250 mL) and brine (250 mL), dried over magnesium sulfate and evaporated under reduced pressure. The crude compound was triturated with hexanes (2 L) for 3 h with stirring. The resulting suspension was left to stand at 0° C. for 5 h and then at −20° C. for 18 h. The solid was filtered and treated again with hexanes (1 L) with stirring for 1 h to give compound 4 which was filtered and dried (190 g, 69%), mp 109–112° C.: $^1$H-NMR δ (300 MHz: $CDCl_3$), 1.5–2.1 (12H, m, O CH—$CH_2$—$CH_2$—$CH_2$—$CH_2$—O), 3.55–3.65 (2H, m, O—CH—$CH_2$—$CH_2$—$CH_2$—$CH_2$O), 3.75–3.95 (2H, m, O—CH—$CH_2$—$CH_2$—$H_2$—$CH_2$O), 4.16 (2H, s, Ph—$CH_2$C═O), 5.40 (1H, t, J=3 Hz, O—CH—$CH_2$—$CH_2$—$CH_2$—$CH_2$—O), 5.49 (1H, t, J=3 Hz, O—CH—$CH_2$—$CH_2$—$CH_2$—$CH_2$—O), 6.55 (1H, dd, J=2.5 Hz and 8.5 Hz, CH phenyl), 6.61 (1H, d, J=2.5 Hz, CH phenyl), 7.03 and 7.17 (2H, AB system, J=8.5 Hz, CH phenyl), 7.77 (1H, d, J=8.5 Hz, CH phenyl), 12.60 (1H, s, Ph OH).

Amine 7

A solution of ditetrahydropyranyl ether 4 (150 g, 0.364 mol), 4-hydroxybenzaldehyde 5 (46 g, 0.377 mol, available from Aldrich Chemical Company Inc., Milwaukee, Wis.) (4-hydroxybenzaldehyde was treated with charcoal and recrystallized with distilled water) and piperidine (11 mL) in benzene (3.7 L) was stirred and refluxed with a Dean-Stark apparatus for 60 h. The solvent was removed under reduced pressure. The crude intermediates, 1-(2-chloroethyl) piperidine monohydrochloride 6 (80 g, 0.435 mol), cesium carbonate (282 g, 0.866 mol) and distilled water (50 mL) in acetone (3.7 L) were mechanically stirred and refluxed for 19 h, and then cooled to room temperature. The mixture was filtered and washed with acetone (100 mL). The filtrate was then removed under reduced pressure to give the residue which was purified by flash chromatography on silica gel (10 L) (ethyl acetate then ethyl acetate: methanol; 9:1) to yield compound 7 (148 g, 65%).

EM-343

To a solution of amine 7 (200 g, 0.319 mol) in dry tetrahydrofuran (3 L) was added methyllithium (1.4M solution in ether, 685 mL, 0.959 mol, available from Aldrich Chemical Company Inc., Milwaukee, Wis.) at −78° C. for 45 min under argon. The cold bath was removed and the reaction mixture was allowed to warm to room temperature over a period of 3 h. The mixture was again cooled to −78° C., and treated with saturated ammonium chloride (1 L). The aqueous solution was extracted with ethyl acetate (2×1 L). The combined organic phase was washed with brine (1 L), dried over magnesium sulfate and evaporated under reduced pressure. The residue was separated in two portions and treated as follows: The residue was dissolved in a mixture of acetic acid (1.6 L) and distilled water (0.2 L) and heated at 90° C. for 30 min under a stream of argon after which it was cooled to room temperature, evaporated under reduced pressure to give the residue which was basified with 15% aqueous sodium carbonate (900 mL). Decantation gave the crude product which was then stirred with a mixture of 15% aqueous sodium carbonate (300 mL) and ethyl acetate (500 mL) for 30 min. The aqueous phase was separated and extracted with ethyl acetate (500 mL). The combined organic phase was washed twice with 15% aqueous sodium carbonate (300 mL) and brine (500 mL), dried over magnesium sulfate and evaporated under reduced pressure to give the product which was purified by flash chromatography on silica gel (6 L) (dichloromethane:ethanol; 9:1) to yield EM-343 (7-hydroxy-3-(4'-hydroxyphenyl)-4methyl-2-(4"-(2'''piperidinoethoxy)phenyl)-2H-benzopyran) (44 g, 60%): $^1$H NMR δ (300 MHz: CD$_3$OD), 1.46 (2H, m, cyclo-N—CH$_2$—CH$_2$—CH$_2$—CH$_2$—CH$_2$), 1.60 (4H, m, cyclo-N—CH$_2$—CH$_2$—CH$_2$—CH$_2$—CH$_2$—), 2.02 (3H, s, CH$_3$—C=C), 2.56 (4H, m, cyclo-N—CH$_2$—CH$_2$—CH$_2$—CH$_2$—CH$_2$—), 2.76 (2H, t, J=5 Hz, O—CH$_2$—CH$_2$—N), 4.06 (2H, t, J=5 Hz, O—CH$_2$—CH$_2$—N), 5.77 (1H, s, O—CH—Ph), 6.12 (1H, d, J=2.5 Hz, CH Phenyl), 6.35 (1H, dd, J=2.5 Hz, 8 Hz, CH Phenyl), 6.70 (2H, d, J=8.5 Hz, CH Phenyl), 6.77 (2H, d, J=8.5 Hz, CH Phenyl), 6.98 (2H, d, J=8.5 Hz, CH Phenyl), 7.12 (1H, d, J=8 Hz, CH Phenyl), 7.19 (2H, d, J=8.5 Hz, CH Phenyl). $^{13}$C NMR δ (75 MHz, CD$_3$OD), 160.0, 159.3, 157.5, 154.6, 133.2, 131.6, 130.5, 125.8, 118.7, 116.1, 115.2, 109.2, 104.5, 81.5, 66.1, 58.8, 55.8, 26.3, 24.9, and 14.9; IR (CHCl$_3$) ν$_{max}$ cm$^{-1}$: 3330, 1607, 1508 and 1231. Mass Spectroscopy: M+457.

SYNTHESIS B, An Alternative Synthesis of EM-343 (This synthesis is described in Schemes 2 and 3 below)

The foregoing synthesis was carried out as follows:

Aldehyde 9

This preparation is reported below in Scheme 2.

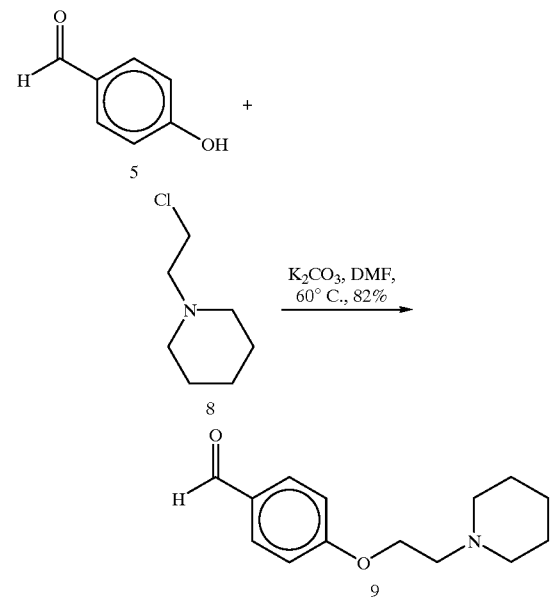

A suspension of 4-hydroxybenzaldehyde 5 (10.0 g, 0.0819 mol), potassium carbonate (22.6 g, 0.164 mol), and 1-(2-chloroethyl)piperidine 8 (18.1 g, 0.123 mol) prepared in 65% yield from 100 g of 1-(2-chloroethyl)piperidine monohydrochloride 6 in anhydrous DMF (40 mL) was heated at 60° C. for 16 h. The reaction mixture was allowed to cool to room temperature, poured into distilled water (200 mL), and extracted with ethyl acetate (3×150 mL). The combined organic phase was washed with saturated sodium bicarbonate (2×100 mL) and brine (3×100 mL) and dried over magnesium sulfate. The crude oil (18 g) was distilled under vacuum [lit (Hugues et al., J. Med. Chem. 7, 511, 1964); bp 147–148° C. (0.05 mm) ] to yield a yellow oil (15.7 g, 82%), which became orange after standing.

SCHEME 3

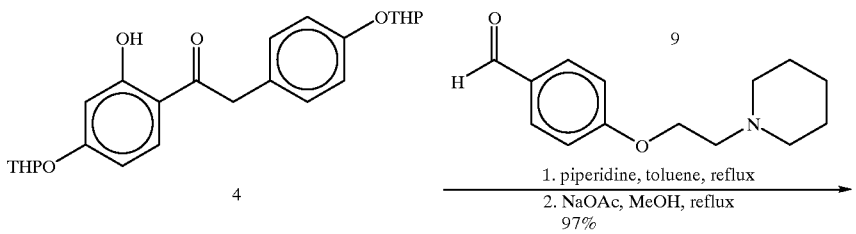

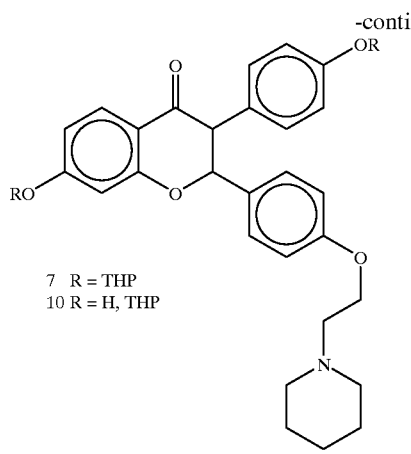

7 R = THP
10 R = H, THP

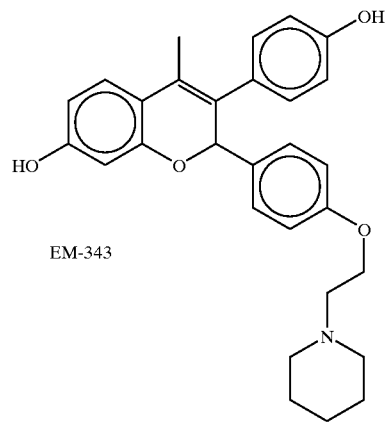

EM-343

Mixture of Amines 7 and 10 (This preparation is reported above in Scheme 3)

A solution of ditetrahydropyranyl ether 4 (5.00 g, 0.0121 mol), aldehyde 9 (2.92 g, 0.0125 mol), and piperidine (0.36 mL, 0.0036 mol) in toluene (120 mL) was stirred and refluxed with a Dean-Stark apparatus for 48 h under argon. The solvent was removed under reduced pressure. The crude intermediates were dissolved in methanol (400 mL), treated with sodium acetate (49 g, 0.60 mol), stirred and refluxed for 18 h, and then cooled to room temperature. The solvent was removed under reduced pressure. The mixture was treated with ethyl acetate (500 mL) and distilled water (500 mL). The aqueous phase was extracted with ethyl acetate (2×100 mL), and the combined organic phase was washed with distilled water (2×100 mL), dried over magnesium sulfate, and evaporated under reduced pressure. The crude products were purified by a flash chromatography on silica gel (ethyl acetate then ethyl acetate: methanol; 9:1) to yield a mixture of amines 7 and 10 (6.8 g, 97%) (mp 78–85° C.).

EM-343 (This preparation is reported above in Scheme 3)

To a solution of amines 7 and 10 (73.0 g, 126 mmol) in dry tetrahydrofuran (1.5 L) was added at 40° C. for 5 min under argon a methylmagnesium bromide solution (3.0 M in ether, 210 mL, 630 mmol) (light precipitate formation). The cold bath was removed and the reaction mixture allowed to warm to room temperature over a period of 3 hours. The mixture was again cooled at −40° C. and treated with saturated ammonium chloride (1 L) and distilled water (500 mL). The aqueous solution was extracted with ethyl acetate (2×1 L). The combined organic phase was washed with brine (1 L), dried over magnesium sulfate, and evaporated under reduced pressure. The residue was dissolved in a mixture of acetic acid (1.05 L) and distilled water (117 mL) and heated from 23° C. to 80° C. in 45 min under a stream of argon. The mixture was then cooled at room temperature and evaporated under reduced pressure (one quarter of initial volume) to give the residue, which was treated with saturated aqueous sodium carbonate (550 mL) (gum formation). Decantation gave the crude product, which was then stirred with a mixture of saturated aqueous sodium carbonate (400 mL) and ethyl acetate (600 mL) for 15 min until complete dissolution. The aqueous phase was separated and extracted with ethyl acetate (500 mL). The combined organic phase was washed twice with saturated aqueous sodium carbonate (200 mL) and brine (300 mL), dried over magnesium sulfate, and evaporated under reduced pressure to give the product, which was purified by flash chromatography on silica gel (dichloromethane:ethanol; 9:1) to afford EM-343 in 62.5% yield.

Example 2

Isolation of (+)-7-hydroxy-3-(4'-hydroxyphenyl)-4-methyl-2(4"-(2'"piperidinoethoxy)phenyl)-2H-benzopyran (EM-652)

The separation of enantiomers of EM-343 (209 g) (see Scheme 4 below) was performed in several runs in 10×50 cm Daicel Chiralpak® ADTM column (available from Chiral Technologies, Inc., Extons, Pa.) at room temperature. The eluent was hexane/ethanol/diethylamine: 80/20/0.02 (by volume). The final products were dried by evaporation at 40° C. under vacuum. The enantiomeric purity was checked by analytical HPLC using Daicel Chiralcel AD™ column (available from Chiral Technologies, Inc., Extons, Pa.) at room temperature and UV detection at 254 nm. The eluent was hexane/ethanol/diethylamine: 80/20/0.2, at flow rate of 1.0 mL/min. In order of elution was obtained:

Fraction 1 (first eluted fraction)

(+)-7-hydroxy-3-(4'-hydroxyphenyl)-4-methyl-2-(4"-(2'"-piperidinoethoxy)phenyl)-2H-benzopyran (EM-652) (92 g, 99.4% ee). $^1$H NMR δ (300MHz: DMSO-$d_6$), 1.33 (2H, m, cyclo-N—$CH_2$—$CH_2$—$CH_2$—$CH_2$—$CH_2$), 1.44 (4H, m, cyclo-N—$CH_2$—$CH_2$—$CH_2$—$CH_2$—$CH_2$—), 2.00 (3H, s, $CH_3$—C=C), 2.35 (4H, m, cyclo-N—$CH_2$—$CH_2$—$CH_2$—$CH_2$—), 2.56 (2H, t, J=5.8 Hz, O—$CH_2$—$CH_2$—N), 3.94 (2H, t, J=5.8 Hz, O—$CH_2$—$CH_2$—N), 5.87 (1H, s, O—CH—Ph), 6.06 (1H, d, J=2.4 Hz, CH Phenyl), 6.31 (1H, dd, J=2.4 Hz and 8. 5 Hz, CH Phenyl), 6.69 (2H, d, J=8.3 Hz, CH Phenyl), 6.77 (2H, d, J=8.6 Hz, CH Phenyl), 7.04 (2H, d, J=8.5 Hz, CH Phenyl), 7.09 (1H, d, J=8.5 Hz, CH Phenyl), 7.17 (2H, d, J=8.6 Hz, CH Phenyl); $^{13}$C NMR δ (75 MHz, DMSO-$d_6$), 158.4, 158.1, 156.3, 152.5, 131.0, 130.3, 129.3, 128.9, 128.2, 124.8, 124.4, 116.6, 115.0, 114.3, 108.1, 103.1, 78.7, 65.4, 57.3, 54.4, 30.6, 25.5 and 23.9; IR ($CHCl_3$) $v_{max}$ cm$^{-1}$: 3372, 1609, 1508 and 1238; $[α]_D^{28}$+129° (c=1.46 THF).

Fraction 2

(−)-7-hydroxy-3-(4'-hydroxyphenyl)-4-methyl-2-(4"-(2'"-piperidinoehtoxy)phenyl)-2H-benzopyran (EM-651) (96 g, 98.4% ee) $[α]_D^{26}$−127° (c 1.08, THF).

SCHEME 4

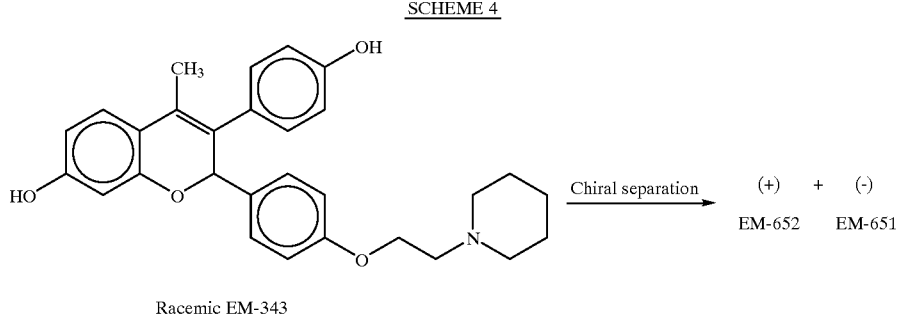

Racemic EM-343

Example 3

Separation of Enantiomers of EM-343 By-Chemical Resolution

A solution of (1S)-(+)-10-camphorsulfonic acid (466 mg, 2.00 mmol) in methanol (20 mL) was added to a solution of EM-343 (918 mg, 2.00 mmol) in methanol (5 ml). The obtained solution was allowed to stand at room temperature for one day and at −20° C. for two days. Scratching was done from time to time to aid crystallization. Crystals were filtered, washed with a minimum of methanol, dried and specific rotation measured ($[\alpha]_D^{25}$+41°, methanol) to give 507 mg of salt. Crystals were recrystallized one or two times if needed in a minimum of hot methanol, in the same condition as above, to give 100 mg of salt ($[\alpha]_D^{25}$+99°, methanol). Mother liquors gave an extra 129 mg of salt ($[\alpha]_D^{25}$+115°).

Example 4

Synthesis of (+)-7-pivaloyloxy-3-(4'-pivaloyloxyphenyl)-4-methyl-2 (4''-(2'''-piperidinoethoxy)phenyl)-2H-benzopyran(EM-800)

SCHEME 5

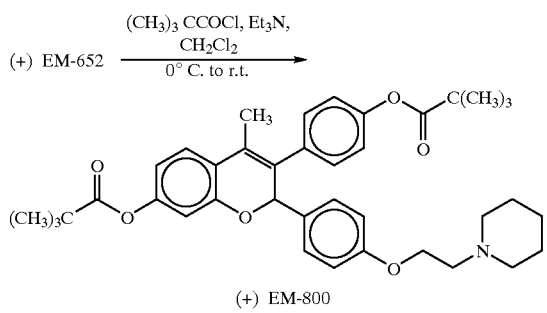

The foregoing synthesis is carried out as follows. A solution of EM-652 (from Scheme 4) ((+)-7-hydroxy-3-(4'hydroxyphenyl)-4methyl-2-(4''-(2'''-piperidinoethoxy)phenyl)-2H benzopyran) (30.8 g, 67.3 mmol) and triethylamine (23.3 mL, 0.168 mol) in dichloromethane (685 mL) was treated with trimethylacetyl chloride (18.1 mL, 0.147 mol, available from Aldrich Chemical Company Inc., Milwaukee, Wis.) at 0° C. under argon. The cold bath was removed and the reaction mixture was allowed to warm to room temperature over a period of 2 h. The mixture was treated with saturated sodium bicarbonate (1 L). The aqueous solution was extracted with dichloromethane (2×1 L). The combined organic phase was dried over magnesium sulfate and evaporated under reduced pressure to give the product which was purified by flash chromatography on silica gel (3 L) (ethyl acetate:hexane 1:1 to ethyl acetate) to yield after recrystallization (isopropanol 2.5 L), EM-800 (37.6 g, 79%). m.p. 167–169° C., $[\alpha]_D^{25}$+87.0° (c=1.0, $CH_2Cl_2$); $^1H$ NMR δ (300 MHz: $CDCl_3$): 1.31 and 1.34 (18H, 2s, t-Bu), 1.42 (2H, m, cyclo-N—$(CH_2)_2$—$CH_2$—$(CH_2)_2$—), 1.58 (4H, m, cyclo-N—$CH_2$—$CH_2$—$CH_2$—$CH_2$—), 2.07 (3H, s, $CH_3$), 2.47 (4H, t def, cyclo-N—$CH_2$—$(CH_2)_3$—$CH_2$—), 2.72 (2H, t, J=6.0 Hz, —N—$CH_2$—$CH_2$—O—), 4.03 (2H, t, J=6.0 Hz, —N—$CH_2$—$CH_2$—O—), 5.85 (1H, s, OCH), 6.48 (1H, d, J=2.3 Hz, CH phenyl), 6.64 (1H, dd, J=2.2, 8.2 Hz, CH phenyl), 6.75 (2H, d, J=8.6 Hz, CH phenyl), 6.99 (2H, d, J=8.4 Hz, CH phenyl), 7.14 (2H, d, J=8.6 Hz, CH phenyl), 7.20 (2H, d, J=8.6 Hz, CH phenyl), 7.28 (1H, d, J=8.2 Hz, CH phenyl); $^{13}C$ NMR δ (75 MHz: $CDCl_3$): 177.0, 176.7, 159.0, 152.8, 151.6, 150.1, 136.0, 130.8, 130.7, 130.2, 129.3, 125.8, 124.3, 122.1, 121.3, 114.5, 113.9, 109.9, 80.1, 77.2, 65.9, 57.9, 55.0, 39.1, 27.1, 26.0, 24.2, 14.7; IR ($CHCl_3$) $\nu_{max}$ $cm^{-1}$: 2938, 1746, 1608, 1508, 1125; anal. calcd for $C_{39}H_{47}NO_6$: C, 74.85; H, 7.57; N, 2.24; found: C, 74.67; H, 7.58; N, 2.34.

Example 5

Synthesis of 7-pivaloyloxy-3-(4'-pivaloyloxy phenyl)-4-methyl-2-(4''(2'''-piperidinoethoxy) phenyl)-2H-benzopyran (EM-762)

The procedure was the same as the synthesis of EM-800, described in Example 4, except that a racemic version of EM-343 was used instead of the optically pure version denoted EM-652.

Example 6

Synthesis of 7-pivaloyloxy -3-(4'-pivaloyloxy phenyl)-4-methyl-2-(4''(2'''-pyrrolidinoethoxy) phenyl)-2H-benzopyran (EM-810)

The procedure was the same as the synthesis of EM-762, described in Examples 1 and 5, except that 1-(2-chloroethyl) pyrrolidine monohydrochloride was used instead of compound 6

Example 7

Synthesis of (+)-7-acyloxy-3-(4'-acyloxyphenyl)-4-methyl-2-(4''-(2'''piperidioethoxy)phenyl)-2H-benzopyran The procedure is the same as the synthesis of EM-800, described in Example 4, except that different acyl halides (chosen depending upon the desired 7 and 4'-substituents in the product) were used instead of trimethylacetyl chloride.

Example 8

Transformation of EM-661 into EM-652. (An example of transforming a prodrug to its active form can, i.e. the form that results in vivo, and the active form can, thereafter, be tested, e.g. by polarimeter, for the proper optical rotation (+) indicative of the desirable absolute configuration at chiral carbon 2).

To a solution of EM-661 (22.5 mg, 0.034 mmol) in anhydrous THF (1.0 mL) was added at −78° C., under an argon atmosphere, a 1.5 M solution of methyl lithium in diethyl ether (0.155 mL, 0.24 mmol), and the mixture was stirred for 40 min. The reaction mixture was then treated with saturated $NH_4Cl$ (2 mL), allowed to warm to room temperature and treated with water (2 mL) and ethyl acetate (5 mL). The aqueous phase was extracted with ethyl acetate (2×5 mL) and combined organic phase was washed with brine, dried, filtered and evaporated to dryness. The residue was chromatographed on silica gel using mixtures of ethanol and methylene chloride (0:100 to 1:9) as eluent and EM-652 (15.5 mg) was obtained in 100% yield. Other carboxylic ester prodrugs may be transformed in an analogous manner.

Example 9

Preparations of Monopivalates of EM-343.

These preparations are described in Schemes 6 and 7.

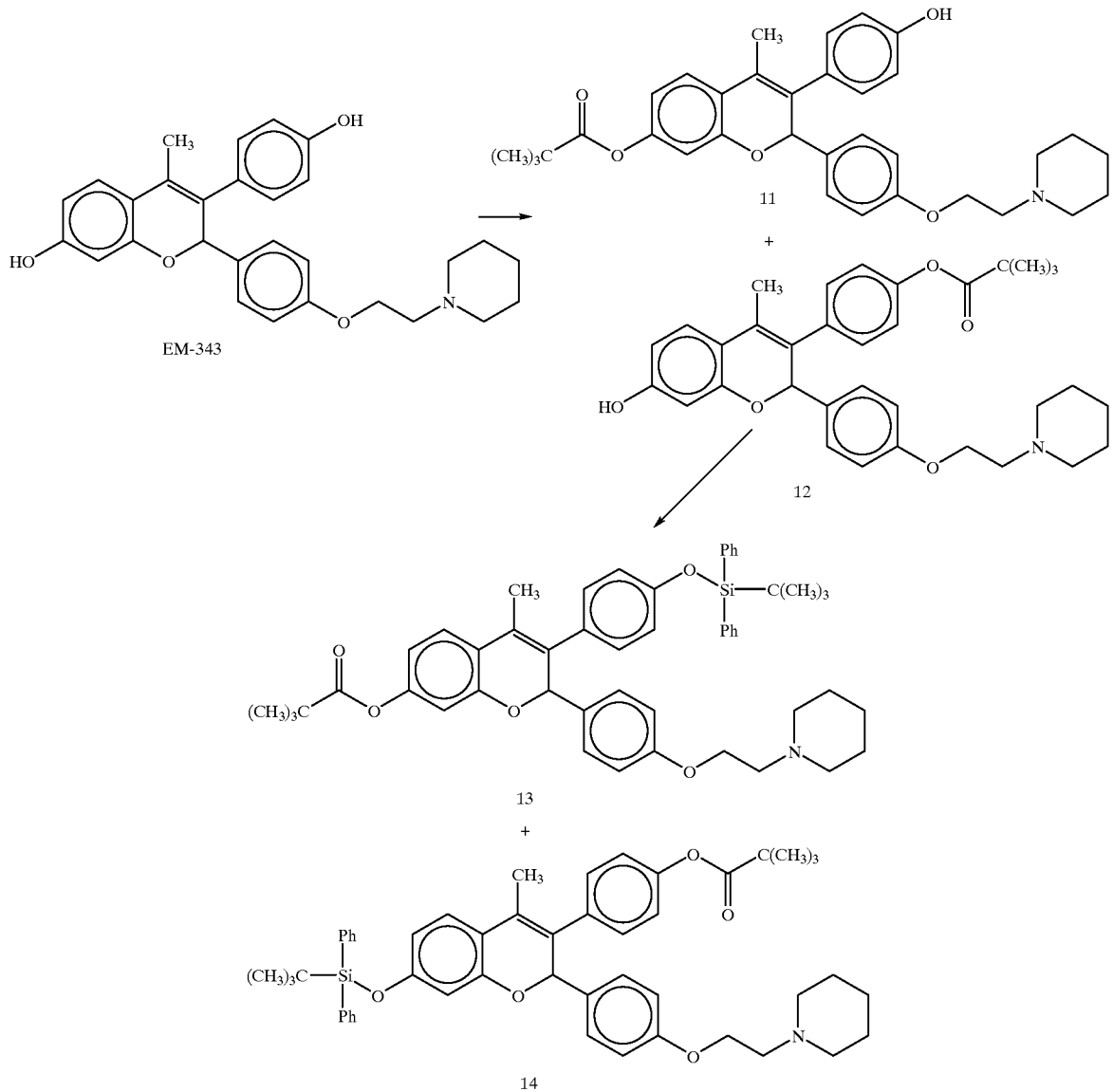

Mixture of Monopivalates of EM-343.

A suspension of EM-343 (from Scheme 1) (7-hydroxy-3-(4'hydroxyphenyl)-4-methyl-2-(4"-(2'"-piperidinoethoxy)phenyl)-2H benzopyran) (114.4 mg, 0.25 mmol) and triethylamine (43.6, μL, 0.313 mmol) in dichloromethane (3.0 mL) was treated with trimethylacetyl chloride (33.9 μl, 0.275 mmol, available from Aldrich Chemical Company Inc., Milwaukee, Wis.) at −78° C. under argon for 20 min. The cold bath was then removed and the reaction mixture was allowed to warm to room temperature over a period of 90 min. The mixture was treated with saturated sodium bicarbonate (5 mL) and dichloromethane (10 mL). The organic phase was washed with saturated sodium bicarbonate (5 mL). The aqueous solution was extracted with ethyl acetate (10 mL). The combined organic phase was washed with a saturated sodium chloride solution (10 mL), dried over magnesium sulfate and evaporated under reduced pressure to give a residue which was purified by flash chromatography on silica gel (pure dichloromethane to 7% methanol in dichloromethane) to yield 52 mg (34% yield) of mixture of compounds 11 and 12.

Silylation of the Mixture of Monopivalates of EM-343.

A solution of mixture of compounds 11 and 12 (50.2 mg, 0.093 mmol), imidazole (7.6 mg, 0.11 mmol) and t-butyldimethylsilyl chloride (15.4 mg, 0.102 mmol, available from Aldrich Chemical Company Inc., Milwaukee, Wis.) ) in anhydrous DMF (1.0 mL) was stirred at room temperature under argon. After 3 hours and 20 hours, imidazole (22.9 mg) and t-butyldimethylsilyl chloride (46.2 mg) were added. After 24 hours, the mixture was treated with distilled water (10 mL) and ethyl acetate (10 mL). The aqueous solution was extracted with ethyl acetate (5 mL). The combined organic phase was washed with saturated sodium chloride solution (3×5 mL), dried over magnesium sulfate and evaporated under reduced pressure to give a residue which was purified by flash chromatography on silica gel (pure dichloromethane to 3% methanol in dichloromethane) to yield the mixture of compounds 13 and 14 (50 mg, 82% yield). This mixture was separated by preparative HPLC using a C-18 NOVA-PAK column 6 μm, 60A (40×100 mm, available from Waters, Mississauga, Ont. Canada) and a UV detector at 214 nm. The eluent was a (90:10) mixture of solution A (10 mM ammonium acetate in methanol) and solution B (10 mM 5 ammonium acetate in water) at a flow rate of 13.0 mL/min. The first eluted peak was, after evaporation of the solvent, the compound 14 and the second was the compound 13.

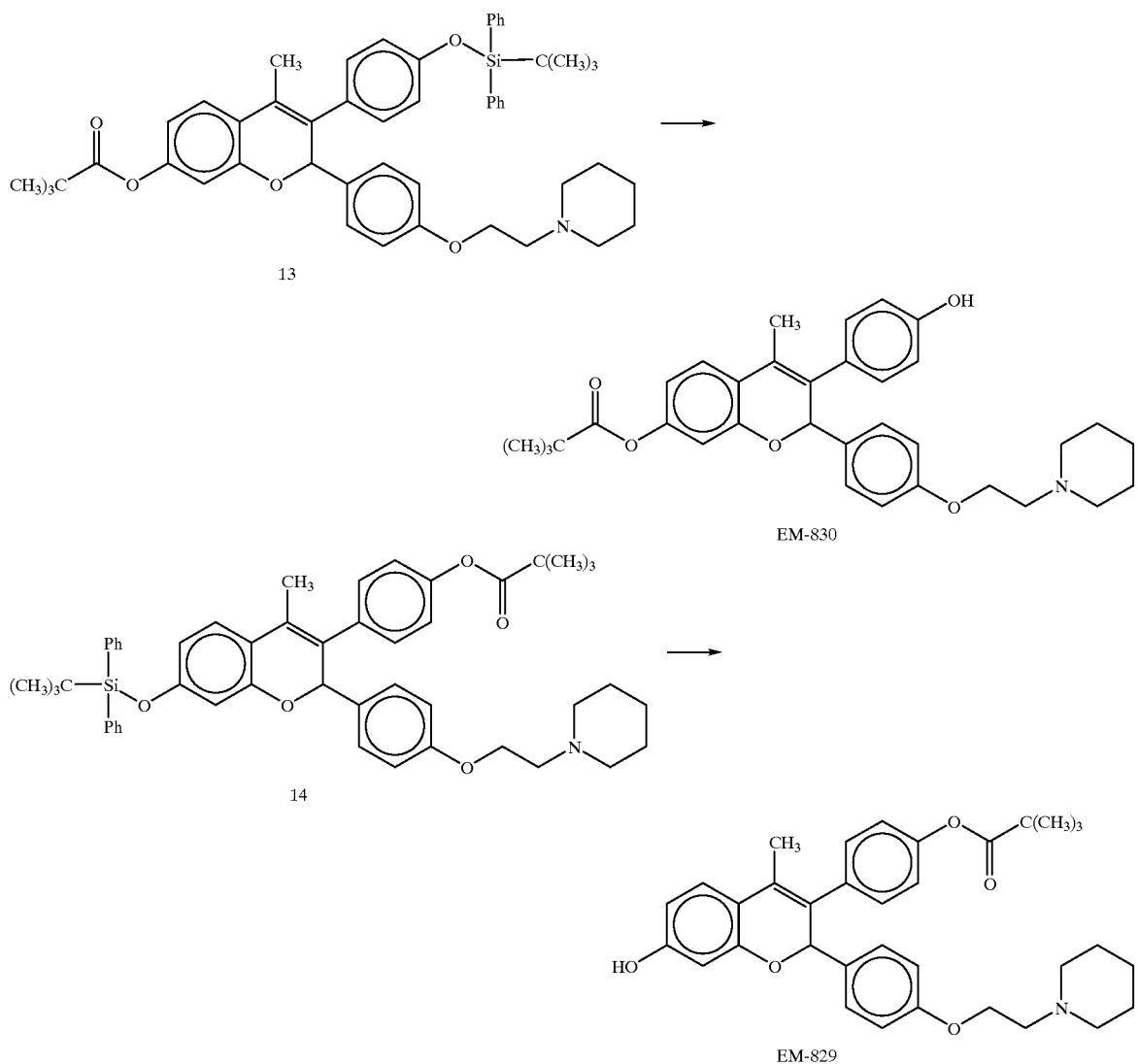

EM-829 (This preparation is described above in the Scheme 7)

A solution of compound 14 (8.4 mg) in 10% HCl in THF (1 mL) was stirred for 4 hours and the mixture was treated with 10% sodium carbonate solution (4 mL) and ethyl acetate (4 mL). The aqueous solution was extracted with ethyl acetate (4 mL). The combined organic phase was washed with a saturated sodium chloride solution (4 mL), dried over magnesium sulfate and evaporated under reduced pressure to give a residue which was purified by flash chromatography on silica gel (pure dichloromethane to 5% methanol in dichloromethane) to yield EM-829 (7-hydroxy-3-(4'-pivaloyloxyphenyl)-4-methyl-2-(4"-(2'"-piperidinoethoxy)phenyl)-2H benzopyran) (2.7 mg); $^1$H NMR δ (300 MHz: CD$_3$OD): 1.32 (9H, s, t-Bu), 1.47 (2H, m, cyclo-N—(CH$_2$)$_2$—CH$_2$—(CH$_2$)$_2$—), 1.61 (4H, m, cyclo-N—CH$_2$—CH$_2$—CH$_2$—CH$_2$—CH$_2$—), 2.05 (3H, s, CH$_3$), 2.54 (4H, t def, cyclo-N—CH$_2$—(CH$_2$)$_3$—CH$_2$—), 2.75 (2H, dd, J=5.5 and 5.7 Hz, —N—CH$_2$—CH$_2$—), 4.06 (2H, dd, 1=5.5 and 5.7 Hz, —N—CH$_2$—CH$_2$—O—), 5.82 (1H, s, OCH), 6.13 (1H, d, J=2.5 Hz, CH phenyl), 6.36 (1H, dd, J=2.5 and 8.5 Hz, CH phenyl), 6.78 (2H, d, J=8.6 Hz, CH phenyl), 6.98 (2H, d, J=8.5 Hz, CH phenyl), 7.18 (5H, m, CH phenyl).

EM-830

In a similar manner EM-830 (7-pivaloyloxy-3-(4'-hydroxyphenyl)-4-methyl-2-(4"-(2'"-piperidinoethoxy)phenyl)-2H-benzopyran) (3 mg) was prepared from the compound 13; $^1$H NMR δ (300 MHz: CD$_3$OD): 1.30 (9H, s, t-Bu), 1.47 (2H, m, cyclo-N—(CH$_2$)$_2$—CH$_2$—(CH$_2$)$_2$—), 1.61 (4H, m, cyclo-N—CH$_2$—CH$_2$—CH$_2$—CH$_2$—CH$_2$—), 2.08 (3H, d, J=0.8 Hz, CH$_3$), 254 (4H, m, cyclo-N—CH$_2$—(CH$_2$)$_3$—CH$_2$—), 2.75 (2H, t, J=5.6 Hz, —N—CH$_2$—CH$_2$—O—), 4.06 (2H, t, J=5.6 Hz, —N—CH$_2$—CH$_2$—O—), 5.87 (1H, s, OCH), 6.37 (1H, d, J=2.1 Hz, CH phenyl), 6.61 (1H, dd, J=2.5 and 8.5 Hz, CH phenyl), 6.72 (2H, d, J=8.6 Hz, CH phenyl), 6.78 (2H, d, J=8.8 Hz, CH phenyl), 7.02 (2H, d, J=8.6 Hz, CH phenyl), 7.21 (2H, d, J=8.6 Hz, CH phenyl), 7.32 (1H, d, J=8.3 Hz, CH phenyl).

Example 10

Synthesis of 7-ethyloxycarbonyloxy-3-(4'-ethyloxycarbonyloxy-phenyl) 4-methyl-2-(4"-(2'"-piperidinoethoxy)phenyl)-2H-benzopyran (CS 119)

To a stirred solution of EM-343 (250 mg, 0.55 mmol) in methylene chloride (5 mL) and pyridine (130 μL) was added dropwise ethylchloroformate (120 μL), over a period of 30 min following the known procedure (F. Reber and T. Reichstein, Helv. Chim. Acta, 28, 1164, 1945). After stirring for 24 h, ethyl chloroformate (120 μL) and pyridine (130 μL) was added again to complete the reaction and then the mixture was washed with saturated NaHCO$_3$ solution and extracted with methylene chloride. The organic phase was washed with brine, dried, and evaporated to dryness. The residue was purified by column silica gel chromatography using a mixture of CH$_2$Cl$_2$: EtOH (9.75: 0.25) as eluent.

Example 11

Synthesis of 7-mesyloxy-3-(4'-mesyloxyphenyl)-4-methyl-2-(4'-(2'"piperidinoethoxy)phenyl)-2H-benzopyran (CS-120)

The procedure was the same as the synthesis of EM-800 which is described in the Example 4 except that mesyl chloride was used instead of trimethylacetyl chloride and racemic EM-343 instead of optically active EM-652.

Example 12

Synthesis of 7-hydroxy-3-(4'-ethoxphenyl)-4-methyl-2-(4'(2'"piperidinoethoxy)phenyl)-2H-benzopyran The synthesis of this compound is similar to the procedure described in the Example 1 except that 4-ethoxyphenylacetic acid (available from Aldrich Chemical Company Inc., Milwaukee, Wis.) is used instead of acid 2.

Example 13

Example of Synthesis of Salts of the Preferred Antiestrogenic Compounds.

The compounds of the following structure have been synthesized by the method described below:

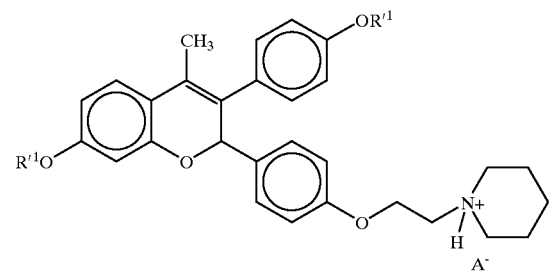

Referring to the chart below, a solution of free amine (1 eq) and acid (1 eq) in the solvent indicated was stirred overnight at room temperature. The reaction mixture was evaporated and recrystallized to give the desired salt.

| Salt | Free amine (amount, mg) | Acid | R'$^1$ | Solvent | Concentration of amine (mmol/L) | Recrystallization solvent | Yield (%) |
|---|---|---|---|---|---|---|---|
| EM-769 | EM-661 (99.9) | A | b | acetone CH$_2$Cl$_2$ (1:1) | 0.050 | — | 100 |
| EM-767 | EM-661 (33.3) | B | b | acetone CH$_2$Cl$_2$ (1:1) | 0.050 | — | 100 |
| EM-778 | EM-661 (33.3) | C | b | acetone CH$_2$Cl$_2$ (1:1) | 0.050 | — | 100 |
| EM-792 | EM-800 (150) | B | c | acetone | 0.034 | ethyl acetate | 33 |
| EM-793 | EM-800 (150) | C | c | acetone | 0.050 | isopropanol | 27 |
| CS-143 | EM-652 (150) | C | a | acetone | 0.050 | ethanol | 66 |
| EM-796 | EM-652 (150) | B | a | acetone | 0.050 | — | 100 |

A (1R)-(−)-10-camphorsulfonic acid
B L-Tartaric acid
C (1S)-(+)-10-camphorsulfonic acid
a H
b C$_6$H$_5$CO
c t-BuCO

Example 14

Synthesis of (+)-7-hydroxy-3-(4'-hydroxyphenyl)-4-methyl-2-(4"-(2'"piperidinoethoxy)phenyl)-2H-benzopyran-4',7-sodium sulfate To a solution of sulfur trioxide in pyridine (prepared from 0.4 mL of SO$_3$ and 20 mL of pyridine and mixed at −20° C.)

is added at room temperature, under an atmosphere of argon, a solution of EM-652 (1.9 g, 4 mmol) in pyridine (10 mL). The mixture is stirred for 7 hours and then water (0.8 mL) and methanol (45 mL) are added. By addition of a methanolic solution of sodium methylate, pH 10.5 is obtained and the mixture is then stirred for another 7 hours, neutralized with a solution of HCl in methanol, filtered and evaporated at 55° C. The residue is dissolved in pyridine and precipitated with ether to obtain the sodium sulfate derivative of EM-652.

Example 15

Synthesis of (+)-7-hydroxy-3-(4'-hydroxyphenyl)-4-methyl-2-(4"-(2'''piperidinoethoxy)phenyl)-2H-benzopyran4',7-disulphamate Sodium hydride (9 mmol, 60% dispersion) and sulfamoyl chloride (1 g, 9 mmol) are added to a stirred solution of EM-652 (1.9 g, 4 mmol) in anhydrous DMF at 0° C. The reaction is allowed to warm to room temperature and then, stirred for 24 hours. The reaction mixture is then poured in cold saturated solution of sodium bicarbonate and the compound is extracted with ethyl acetate. The combined organic extracts are dried, filtered and evaporated to dryness. The residue is further purified by silica gel flash chromatography using mixtures of hexane, ethyl acetate and methanol as eluent.

Example 16

Synthesis of (+)-7-hydroxy-3-(4'-hydroxyphenyl)-4-methyl-2-(4"-(2'''piperidinoethoxy)phenyl)-2H-benzopyran-4',7-di(methyl phosphonate), sodium salt To a stirred solution of EM-652 (1.9 g, 4 mmol) in anhydrous pyridine (10 mL) is added dropwise methylphosphonic dichloride (1.2g, 9 mmol) (available from Aldrich Chemical Company Inc., Milwaukee, Wis.) in anhydrous pyridine (20 mL) at 0° C. under argon. The reaction mixture is allowed to warm to room temperature and stirring is continued for an additional 24 hours. The mixture is then cooled to 0° C. and water (10 mL) is added dropwise. The reaction mixture is allowed to warm to room temperature and stirring is continued for an additional 12 hours. By addition of a methanolic solution of sodium hydroxy, pH 10.5 is obtained and the mixture is then stirred for 7 hours, neutralized with a solution of HCl in methanol, evaporated at 550° C. The residue is dissolved in pyridine and precipitated with ether to obtain the sodium phosphonate derivative of EM-652.

Example 17

Synthesis of (+)-7-hydroxy-3(4'-hydroxyphenyl)-4methyl-2-(4"-(2'''piperidinoethoxy)phenyl)-2H-benzopyran-4",7di(methylthiophosphonate), sodium salt.

To a stirred solution of EM-652 (1.9 g, 4 mmol) in anhydrous pyridine (10 mL) is added dropwise methylthiophosphonic dicldoride (0.94 mL) (available from CN Biochemicals Ltd., High Wycombe, Bucks, U.K.) in anhydrous pyridine (20 mL) at 0° C. under argon. The reaction mixture is allowed to warm to room temperature and stirring is continued for an additional 24 hours. The mixture is then cooled to 0° C. and water (10 mL) is added dropwise. The reaction mixture is allowed to warm to room temperature and stirring is continued for an additional 12 hours. By addition of a methanolic solution of sodium hydroxy, pH 10.5 is obtained and the mixture is then stirred for 7 hours, neutralized with a solution of HCl in methanol, evaporated at 55° C. The residue is dissolved in pyridine and precipitated with ether to obtain sodium thiophosphonate derivative of EM-652.

Other compounds within the scope of the invention may be synthesized by methods analogous to those described in Examples 1–17, and Examples 1–17 may be modified by techniques that are known in the art, to result in the other compounds within the scope of the invention.

Set forth below, by way of example and not of limitation, are several pharmaceutical compositions utilizing a preferred active compound EM-800. Other compounds of the invention or combination thereof, may be used in place of (or in addition to) EM-800. The concentration and identity of ingredients may be varied over a wide range known in the art.

Example 18

| Composition suitable for injection | |
| --- | --- |
| Ingredient | Weight % (by weight of total composition) |
| EM-800 | 0.4 |
| Ethanol | 6.4 |
| NaCl | 0.8 |
| Water | 91.5 |
| Benzyl alcohol | 0.9 |

Example 19

| Composition suitable for use as topical lotion | |
| --- | --- |
| Ingredient | Weight % (by weight of total composition) |
| EM-800 | 1.0 |
| Ethanol | 70.0 |
| Propylene glycol | 29.0 |

Example 20

| Composition suitable for use as topical gel | |
| --- | --- |
| Ingredient | Weight % (by weight of total composition) |
| EM-800 | 1.0 |
| Kucel | 1.5 |
| Ethanol | 70.0 |
| Propylene glycol | 27.5 |

Example 21

| Ingredient | Weight % (by weight of total composition) |
| --- | --- |
| EM-800 | 1.0 |
| Gelatin | 5.0 |
| Lactose | 67.5 |
| Starch | 26.5 |

Example 22

Gelatin capsule

| Ingredient | Weight % (by weight of total composition) |
| --- | --- |
| EM-800 | 2.0 |
| Lactose hydrous | 80.0 |
| Starch | 4.8 |
| Cellulose microcrystalline | 12.8 |
| Magnesium stearate | 0.4 |

Example 23

Composition suitable for use as topical gel

| Ingredient | Weight % (by weight of total composition) |
| --- | --- |
| EM-800 | 1.0 |
| Ethanol | 4.0 |
| Polyethylene glycol | 4.0 |
| Gelatin | 1.0 |
| NaCl | 0.9 |
| Benzyl alcohol | 1.0 |
| Water USP | 88.1 |

EFFICACY OF THE PREFERRED INHIBITORS

Antiestrogenic activity of some preferred compounds has been measured using the ZR-75-1 human breast cancer cell line as described in more detail below.

Maintenance of Stock Cell Cultures

ZR-75-1 cells (83rd passage) were obtained from the American Type Culture Collection (Rockville, Md.) and routinely cultured in phenol red free RPMI 1640 supplemented with 1 nM estradiol ("E2"), 2 mM L glutamine, 1 mM sodium pyruvate, 15 mM N-2-hydroxyethyl piperazine-N'-2-ethanesulfonic acid, 100 IU penicillin/ml, 100 µg streptomycin/ml, and 10% (v/v) fetal bovine serum (Hyclone, Logan, UT) under a humidified atmosphere of 95% air, 5% $CO_2$, at 37° C. All media and medium supplements were purchased from Sigma. Cells were subcultured weekly by treatment with a pancreatic solution containing EDTA (0.2 g/L). The cell cultures used for the experiments herein described were between passages 89 and 94.

Measurements of Cell Proliferation

Figure 1:
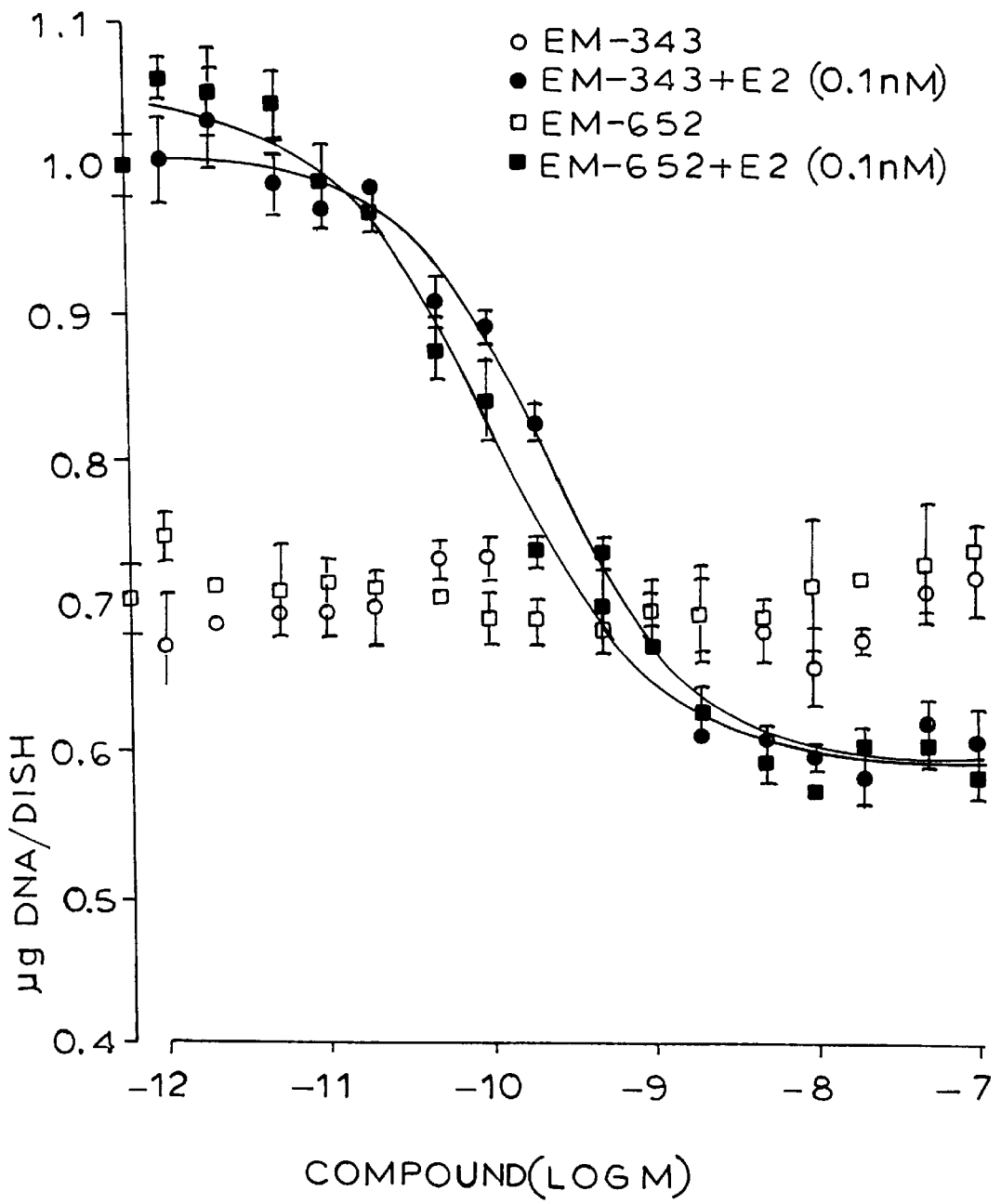
FIG. 1 illustrates the comparative inhibitory activity of increasing concentrations of EM-343

Cells in their logarithmic growth phase were harvested, briefly centrifuged, and resuspended in RPMI 1640. Cells were then plated in triplicate in LIMBRO 24-well plastic culture plates (2 $cm^2$/well). Since plating density influences the effect of hormones on ZR-75-1 cell growth, cells were plated at a density of $1\times10^4$ cells/well. After 72 h, medium was replaced with fresh medium of identical composition, except containing increasing concentrations of inhibitors (e.g. EM-343 (as a racemic mixture) and EM-652 in FIG. 1; EM-612, EM-658, and EM-661 in FIG. 2; and EM-762, EM-800, and EM-776 in FIG. 3) as indicated along the X-axis. Control cultures received the ethanol vehicle only. Cells were then allowed to grow at 37° C. for 10 days with medium changes (of identical composition) every 2 days. In absence of inhibitors, in 0.1 nM estradiol ($E_2$)containing medium, ZR-75-1 cells have doubling time of about 48 h.

After $E_2$ and/or antiestrogen treatment, cells were harvested by addition of 0.5 ml of a pancreatin solution (Sigma) for 5–10 min at 37° C. before addition of 0.5 ml of RPMI 1640 containing 5% dextran coated charcoal-fetal bovine serum in order to block enzymatic action. Cell number (0.10 ml aliquot) was determined by measurement of DNA content as previously described (Simard et al., Endocrinology 126: 3223–3231, 1990). $IC_{50}$ values, which are the concentrations of antiestrogens needed to decrease by 50% the estradiol-stimulated cell growth enhancement, were calculated and are reported herein. Thus the more effective antiestrogen is the lower its $IC_{50}$. As may be seen from FIG. 1, the dextrogyric enantiomer of EM-343, namely EM-652, has a better effectiveness than does racemic EM-343 on the growth of the human ZR-75-1 breast cancer cells, the $IC_{50}$ value of EM-652 being 2-fold lower than for EM-343 ($2.4\times10^{-10}$M versus $1.1\times10^{-10}$M, respectively).

As may be seen from FIG. 2, the dextrogyric enantiomer, EM-661, also has a better effectiveness than racemic EM-612 on the growth of the human ZR-75-1 breast cancer cells. The levogyric enantiomer EM-658 has only a weak effectiveness, the $IC_{50}$ from EM-658 being more than 69-fold higher. In FIG. 3, the dextrogyric enantiomer EM-800 is also more active than the racemic EM-762 and the levogyric enantiomer EM-776 has only a weak effectiveness.

In vivo antiestrogenic activity of preferred antiestrogens was measured as by determining a test compound's ability to inhibit the estradiol-induced stimulation of uterine weight in adult female ovariectomized Balb/c mice (body weight= 19–20 g) sacrificed five days after ovariectomy. Preferred antiestrogens dissolved in ethanol were orally administered in the appropriate groups in a solution of sodium chloride (9 g/L), gelatin (10 g/L), 4% (v/v) ethanol and 4% polyethylene glycol (PEG600) at indicated concentrations. A dosage of 02 ml of the foregoing preparation, was administered once daily from day 3 to day 11 after ovariectomy. Estrone was injected at a dose of 0.06 µg in 0.2 ml, twice daily, starting on day 6 after ovariectomy for a total of 12 injections. After sacrifice, the uteri were rapidly removed, freed from fat and connective tissue and weighed.

As shown in FIG. 4 the antiestrogenic activity of EM-343 (when in racemic form), its dextrogyric enantiomer EM-652 and its levogyric enantiomer EM-651 are reported as the means±SEM of groups of 9–10 mice. EM-652 was more effective by a 2-fold magnitude in reducing estradiol-induced uterine weight gain than was racemic EM-343, while the levogyric enantiomer EM-651 had only weak activity.

As shown in FIG. 5, the antiestrogenic activity of racemic EM-762, its dextrogyric enantiomer EM-800, and its levogyric enantiomer EM-776 are reported as the means±SEM of groups of 9–10 mice. EM-800 was more effective in reducing estradiol-induced uterine weight gain than the racemic EM-762. The levogyric enantiomer EM-776 had only weak activity. Additional effectiveness data are set forth below in Table 1 and Table 2. Percent inhibition is reported for various compounds tested using the foregoing techniques.

TABLE 1

| Name of Compounds | $R'^1$ | $R_3, R_4$ | $[\alpha]_D$ (Temp., Conc. % Solvant) | % of inhib. on mice uteri (7.5 nmol, per os, i.d.) |
|---|---|---|---|---|
| EM-612 | $C_6H_5CO$ | —$(CH_2)_5$— | dl | 62.0 ± 6.3 |
| EM-611 | o-MeOΦCO | —$(CH_2)_5$— | dl | 71.8 ± 8.2 |
| EM-617 | o-ClΦCO | —$(CH_2)_5$— | dl | 63.5 ± 5.2 |
| EM-618 | p-ClΦCO | —$(CH_2)_5$— | dl | 74.9 ± 6.1 |
| EM-622 | o-AcOΦCO | —$(CH_2)_5$— | dl | 66.6 ± 6.6 |
| EM-626 | p-MeOΦCO | —$(CH_2)_5$— | dl | 66.5 ± 4.3 |
| EM-628 | m-MeOΦCO | —$(CH_2)_5$— | dl | 81.3 ± 7.9 |
| EM-753 | R-camphor-sulfonate | —$(CH_2)_5$— | n/a | 6.5 ± 0.3 |
| EM-757 | p-$NO_2$ΦCO | —$(CH_2)_5$— | dl | 60.8 ± 2.2 |
| EM-758 | p-CNΦCO | —$(CH_2)_5$— | dl | 65.5 ± 4.9 |
| EM-762 | t-BuCO | —$(CH_2)_5$— | dl | 63.5 ± 3.7 |
| EM-773 | $CH_3CO$ | —$(CH_2)_5$— | dl | n/a |
| EM-770 | $C_2H_5SO_2$ | —$(CH_2)_5$— | dl | 1.05 ± 0.04 |
| EM-771 | i-$C_3H_7CO$ | —$(CH_2)_5$— | dl | 61.8 ± 2.4 |
| EM-772 | $(CH_3)_2NCO$ | —$(CH_2)_5$— | dl | 55.1 ± 2.4 |
| EM-652 | H | —$(CH_2)_5$— | +129° (28, 1.46, THF) | 68.1 ± 6.5 |
| EM-651 | H | —$(CH_2)_5$— | −127° (26, 1.08, THF) | 0 |
| EM-658 | $C_6H_5CO$ | —$(CH_2)_5$— | −82° | 0 |
| EM-661 | $C_6H_5CO$ | —$(CH_2)_5$— | +81° (25, 0.14, $CHCl_3$) | 38.7 ± 2.5 |
| CS-119 | $C_2H_5OCO$ | —$(CH_2)_5$— | dl | 60.7 ± 6.3 |
| CS-120 | $CH_3SO_2$ | —$(CH_2)_5$— | dl | 1.9 ± 0.1 |
| CS-121 | $CH_3OCO$ | —$(CH_2)_5$— | dl | 58.4 ± 4.3 |
| CS-122 | $C_2H_5SCO$ | —$(CH_2)_5$— | dl | 71.5 ± 3.5 |
| EM-800 | t-BuCO | —$(CH_2)_5$— | +87° (25, 1.0, $CH_2Cl_2$) | 81.1 ± 7.4 |
| EM-776 | t-BuCO | —$(CH_2)_5$— | −93° (26, 1.0, $CH_2Cl_2$) | 4.5 ± 0.3 |
| EM-775 | $CF_3$ΦCO | —$(CH_2)_5$— | dl | 73.1 ± 5.1 |
| EM-801 | cyclo $C(CH_3)$—$C_2H_4CO$ | —$(CH_2)_5$— | — | |
| EM-810 | t-BuCO | —$(CH_2)_4$— | — | |

TABLE 2

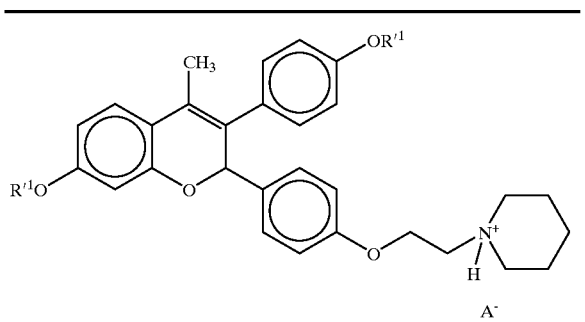

Where "A⁻" represents the corresponding anion of the acid AH

| Name of Compounds | R'¹ | AH | $[\alpha]_D$ (Temp., Conc. % Solvent) | % of inhib. on mice uteri (7.5 nmol, per os, i.d.) |
|---|---|---|---|---|
| EM-767 | $C_6H_5CO$ | L-tartaric | +76° (26, 0.21, THF) | 61.9 ± 1.2 |
| EM-769 | $C_6H_5CO$ | R-camphorsulfonic | +57.8° (26, 0.8, $CH_2Cl_2$) | 78.6 ± 3.2 |
| EM-778 | $C_6H_5CO$ | S-camphorsulfonic | +92° (26, 0.48, THF) | 73.1 ± 6.7 |
| EM-792 | t-BuCO | L-tartaric | +89° (26, 1.0, THF) | 63.6 ± 1.6 |
| EM-793 | t-BuCO | R-camphorsulfonic | +88° (26, 1.17, THF) | 77.2 ± 4.1 |
| EM-796 | H | L-tartaric | — | 75.8 ± 6.5 |
| CS-143 | H | S-camphorsulfonic | +120° (26, 1.0, THF) | — |

The terms and descriptions used herein are preferred embodiments set forth by way of illustration only, and are not intended as limitations on the many variations which those of skill the art will recognize to be possible in practicing the present invention as defined by the claims.

What is claimed is:

1. An optically active compound or pharmaceutically acceptable salt thereof, said compound having the molecular structure:

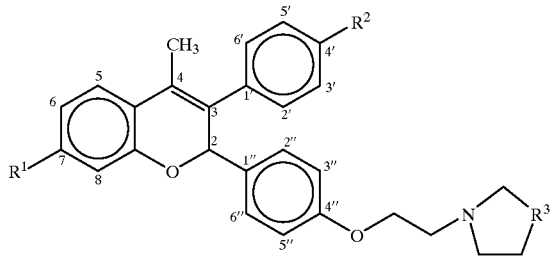

wherein $R^1$ and $R^2$ are independently selected from the group consisting of hydroxyl and a moiety convertible in vivo to hydroxyl;
wherein $R^3$ is —$CH_2$— or —$CH_2CH_2$—; and
wherein stereoisomers that have the following absolute configuration:

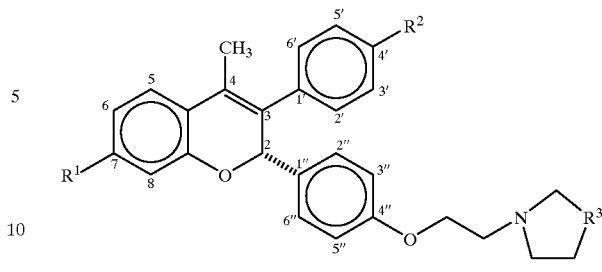

are present in an amount higher than 50% by weight relative to all stereoisomers present.

2. The compound or salt of claim 1, wherein said stereoisomers that have said absolute configuration are present at a concentration above 90% by weight relative to all stereoisomers.

3. The compound or salt of claim 1, wherein said compound or salt substantially lacks stereoisomers that do not have said absolute configuration.

4. The compound or salt of claim 1, wherein $R^3$ is —$CH_2CH_2$— and wherein at least one of $R^1$ or $R^2$ is selected from the group consisting of aliphatic and aromatic acyloxy.

5. The compound or salt of claim 1, wherein at least one of $R^1$ or $R^2$ is selected from the group consisting of acyloxy,

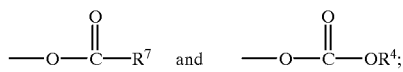

wherein $R^4$ is selected from the group consisting of alkyl, alkenyl, alkynyl and aryl; and $R^7$ is selected from the group consisting of amino, alkylamino, aminoalkyl and alkyl sulfanyl.

6. The compound or salt of claim 1, wherein at least one of $R^1$ or $R^2$ is acyloxy.

7. The compound or salt of claim 1, wherein at least one of $R^1$ or $R^2$ is aromatic or aliphatic acyloxy.

8. The compound or salt of claim 1, wherein at least one of $R^1$ or $R^2$ is a hindered aliphatic acyloxy.

9. The compound or salt of claim 1, wherein at least one of $R^1$ or $R^2$ is pivaloyloxy.

10. The optically active compound or salt of claim 1, said compound having the following molecular structure:

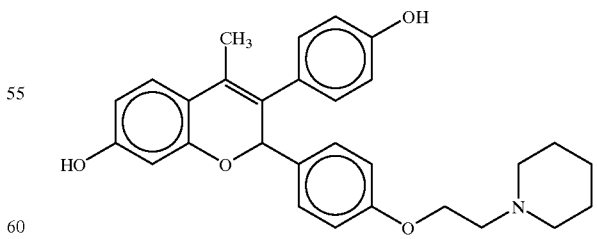

11. The optically active compound or salt of claim 1, said compound having the following molecular structure:

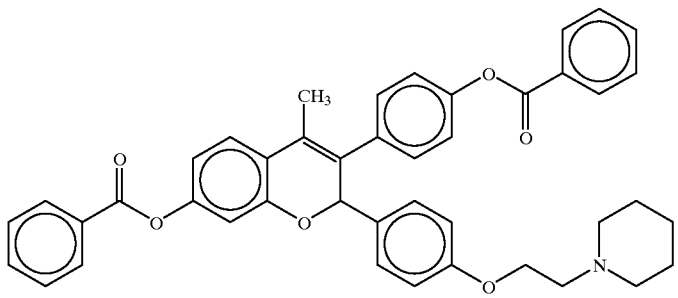

12. The optically active compound or salt of claim 1, said compound having the following molecular structure:

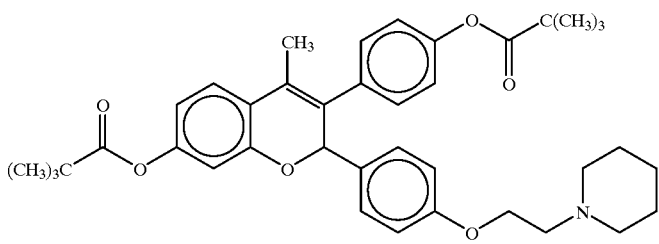

13. A compound of the following molecular structure:

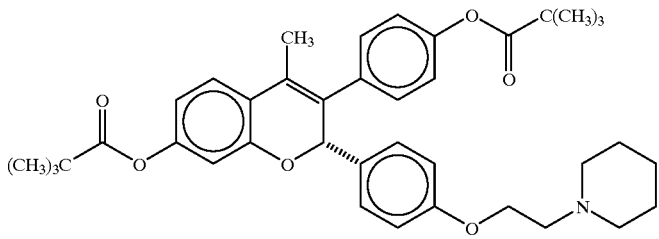

14. A compound or pharmaceutically acceptable further salt thereof, said compound having the molecular structure:

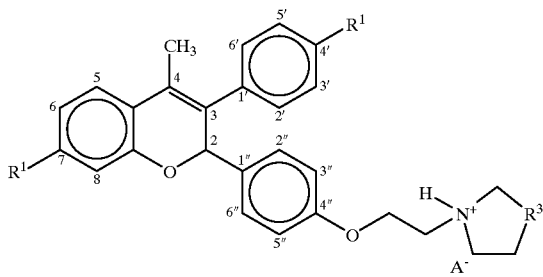

wherein A- is an anion of a pharmaceutically acceptable acid;

wherein $R^1$ and $R^2$ are independently selected from the group consisting of hydroxyl and a moiety convertible in vivo to hydroxyl; and wherein $R^3$ is —$CH_2$— or —$CH_2CH_2$—.

15. A compound or further salt of claim 14, wherein said compound or salt is optically active and includes more than 50% (by weight relative to all stereoisomers) of stereoisomers that have the following absolute configuration:

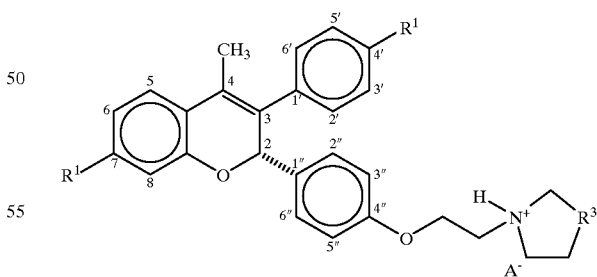

16. The compound or further salt of claim 14, wherein $R^3$ is —$CH_2$—$CH_2$—;

wherein at least one of $R^1$ or $R^2$ is selected from the group consisting of aliphatic and aromatic acyloxy; and wherein A- is an anion of an acid selected from the group consisting of acetic acid, adipic acid, benzenesulfonic acid, benzoic acid, camphorsulfonic acid, citric acid , at a purity such that any 2R-stereoisomer thereof that may be present as an impurity is present at less than 10% by weight relative to all stereoisomers.

fumaric acid, hydroiodic acid, hydrobromic acid, hydrochloric acid, hydrochlorothiazide acid, hydroxynaphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-tuluenesulfonic acid, and valeric acid.

17. The compound or further salt of claim 15, wherein said stereoisomer having said absolute configuration is present at a concentration above 90% (by weight relative to all stereoisomers).

18. The compound or further salt of claim 15, wherein said compound or salt substantially lacks stereoisomers other than those having said absolute configuration.

19. The compound or further salt of claim 14, wherein at least one of $R^1$ or $R^2$ is acyloxy or is selected from the group consisting of:

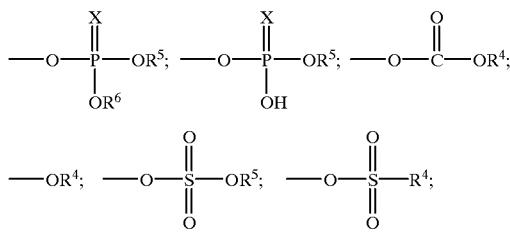

-continued

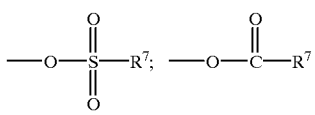

wherein X is sulfur or oxygen;

$R^4$ is selected from the group consisting of alkyl, alkenyl, alkynyl and aryl;

$R^5$ and $R^6$ are independently selected from the group consisting of hydrogen, alkyl, alkenyl, alkynyl, aryl and a cation; and $R^7$ is selected from the group consisting of amino, alkylamino, aminoalkyl, and alkylsulfanyl.

20. The compound or further salt of claim 14, wherein at least one of $R^1$ or $R^2$ is acyloxy.

21. The compound or further salt of claim 14, wherein at least one of $R^1$ or $R^2$ is selected from the group consisting of aliphatic and aromatic acyloxy.

22. The compound or further salt of claim 20, wherein at least one of $R^1$ or $R^2$ is a hindered aliphatic acyloxy.

23. The compound or further salt of claim 20, wherein said acyloxy is pivaloyloxy.

24. The optically active compound of claim 15, wherein said compound is selected from the group consisting of:

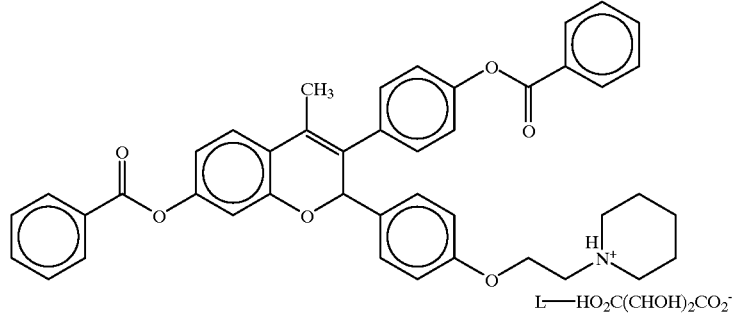

and

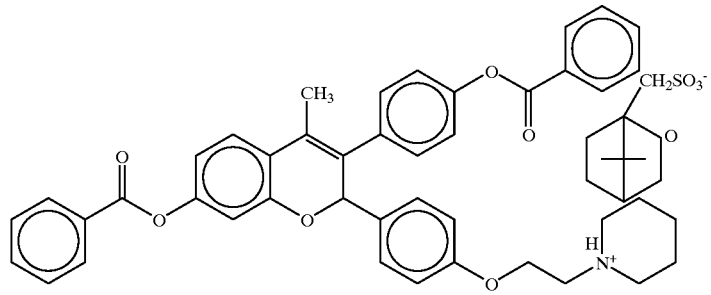

25. The optically active compound of claim 15, wherein said compound is selected from the group consisting of:

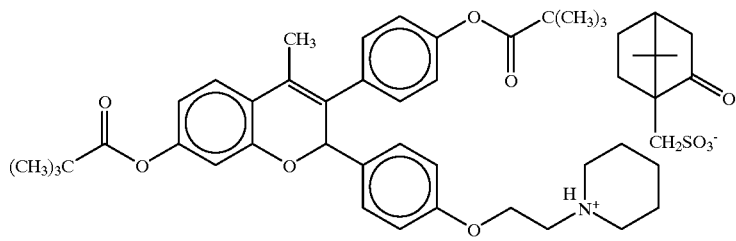

and

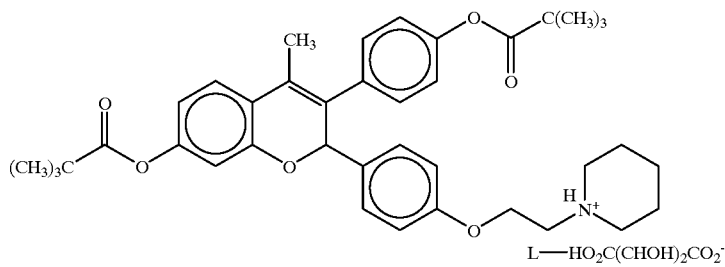

26. The optically active compound of claim 15, having the following molecular structure:

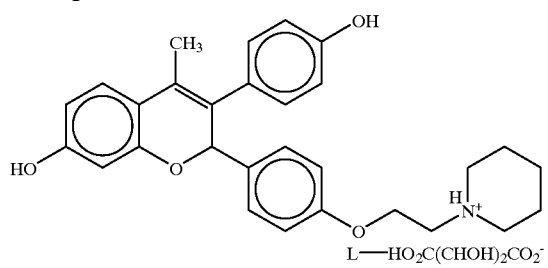

27. A compound or pharmaceutically acceptable salt thereof, having the molecular structure:

I

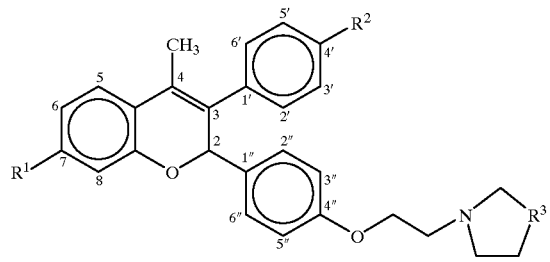

wherein $R^3$ is —$CH_2$— or —$CH_2CH_2$—; and wherein $R^1$ and $R^2$ are independently selected from the group consisting of hydroxy, alicyclic or branched aliphatic acyloxy, and

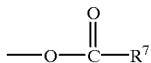

wherein $R^7$ is selected from the group consisting of amino, alkylamino, aminoalkyl, alkylsulfanyl, alkoxy, alkenyloxy and alkynyloxy;

wherein at least one of $R^1$ or $R^2$ is not hydroxy.

28. The compound or salt of claim 27, wherein at least one of $R^1$ or $R^2$ is a branched alicyclic or aliphatic acyloxy.

29. The compound or salt of claim 27, wherein at least one of $R^1$ or $R^2$ is pivaloyloxy.

30. The compound or salt of claim 27, wherein said compound is selected from the group consisting of:

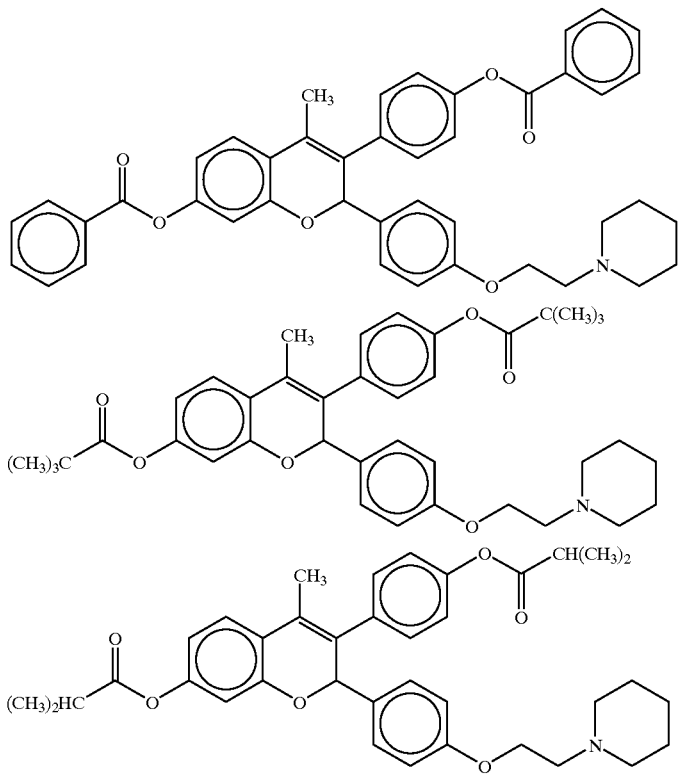

and pharmaceutically acceptable salts of any of the foregoing compounds.

31. A pharmaceutical composition comprising a therapeutically acceptable amount of an optically active compound or pharmaceutically acceptable salt thereof, said compound having the molecular structure:

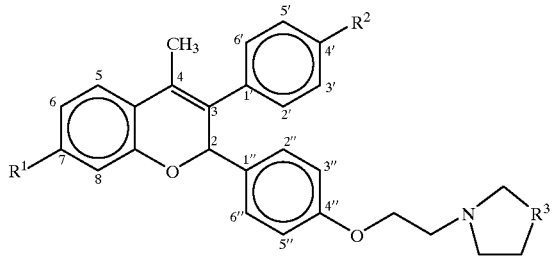

wherein $R^1$ and $R^2$ are independently selected from the group consisting of hydroxyl and a moiety convertible in vivo to hydroxyl;

wherein $R^3$ is —CH$_2$— or —CH$_2$CH$_2$—; and wherein stereoisomers that have the following absolute configuration:

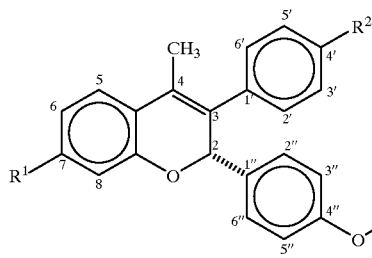

are present in an amount higher than 50% by weight relative to all stereoisomers present.

32. The pharmaceutical composition of claim 31, wherein said stereoisomers that have said absolute configuration are present at a concentration above 90% by weight relative to all stereoisomers.

33. The pharmaceutical composition of claim 31, wherein said compound or salt substantially lacks stereoisomers that do not have said absolute configuration.

34. The pharmaceutical composition of claim 31, wherein $R^3$ is —CH$_2$CH$_2$— and wherein at least one of $R^1$ or $R^2$ is selected from the group consisting of aliphatic and aromatic acyloxy.

35. The pharmaceutical composition of claim 31, wherein at least one of $R^1$ or $R^2$ is selected from the group consisting of acyloxy,

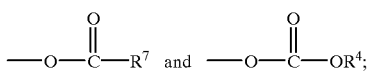

wherein $R^4$ is selected from the group consisting of alkyl, alkenyl, alkynyl and aryl; and $R^7$ is selected from the group consisting of amino, alkylamino, aminoalkyl and alkyl sulfanyl.

36. The pharmaceutical composition of claim 31, wherein at least one of $R^1$ or $R^2$ is acyloxy.

37. The pharmaceutical composition of claim 31, wherein at least one of $R^1$ or $R^2$ is aromatic or aliphatic acyloxy.

38. The pharmaceutical composition of claim 31, wherein at least one of $R^1$ or $R^2$ is a hindered aliphatic acyloxy.

39. The pharmaceutical composition of claim 31, wherein at least one of $R^1$ or $R^2$ is pivaloyloxy.

40. The pharmaceutical composition of claim 31, wherein said compound has the following molecular structure:

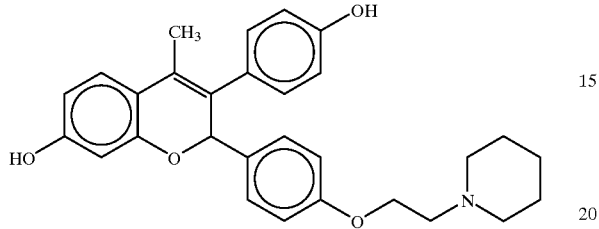

41. The pharmaceutical composition of claim 31, wherein said compound has the following molecular structure:

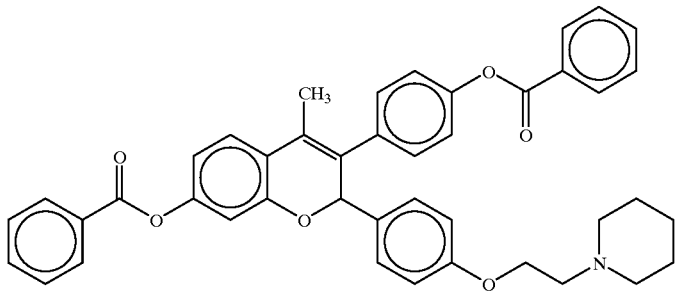

42. The pharmaceutical composition of claim 31, wherein said compound has the following molecular structure:

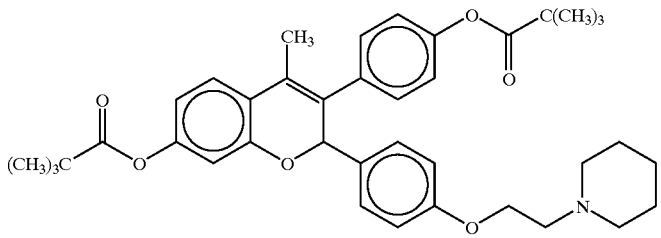

43. A pharmaceutical composition comprising a pharmaceutically acceptable diluent or carrier and a therapeutically acceptable amount of a compound of the following molecular structure:

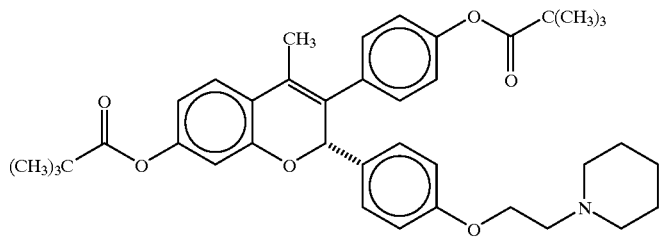

at a purity such that any 2R-stereoisomer thereof that may be present as an impurity is present at less than 10% by weight relative to all stereoisomers.

44. A pharmaceutical composition comprising a pharmaceutically acceptable diluent or carrier and a therapeutically acceptable amount of a compound or pharmaceutically acceptable further salt thereof, said compound having the molecular structure:

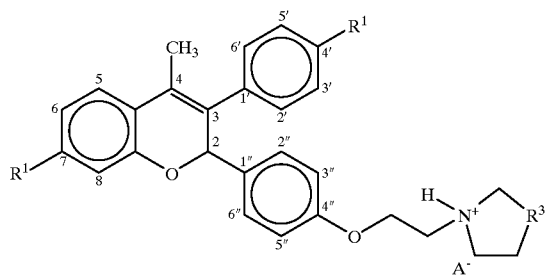

wherein A– is an anion of a pharmaceutically acceptable acid;

where in $R^1$ and $R^2$ are independently selected from the group consisting of hydroxyl and a moiety convertible in vivo to hydroxyl; and wherein $R^3$ is —CH$_2$— or —CH$_2$CH$_2$—.

45. The pharmaceutical composition of claim 44, wherein said compound or salt is optically active and includes more than 50% (by weight relative to all stereoisomers) of stereoisomers that have the following absolute configuration:

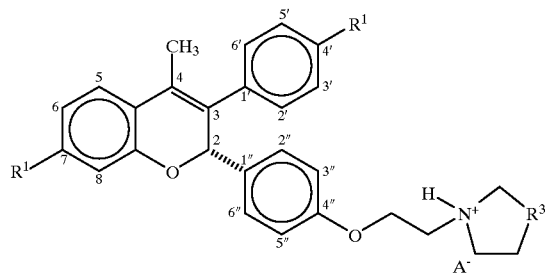

46. The pharmaceutical composition of claim 44, wherein $R^3$ is —CH$_2$CH$_2$—;

wherein at least one of $R^1$ or $R^2$ is selected from the group consisting of aliphatic and aromatic acyloxy; and wherein A– is an anion of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxynaphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-tuluenesulfonic acid, and valeric acid.

47. The pharmaceutical composition of claim 45, wherein said stereoisomer having said absolute configuration is present at a concentration above 90% (by weight relative to all stereoisomers).

48. The pharmaceutical composition of claim 45, wherein said compound or salt substantially lacks stereoisomers other than those having said absolute configuration.

49. The pharmaceutical composition of claim 44, wherein at least one of $R^1$ or $R^2$ is acyloxy or is selected from the group consisting of:

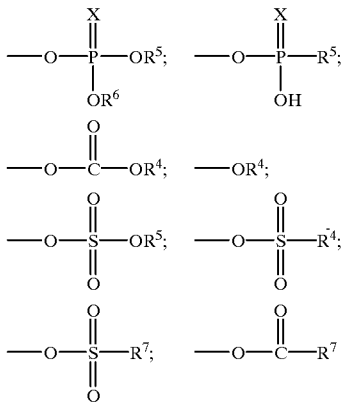

wherein X is sulfur or oxygen;

$R^4$ is selected from the group consisting of alkyl, alkenyl, alkynyl and aryl;

$R^5$ and $R^6$ are independently selected from the group consisting of hydrogen, alkyl, alkenyl, alkynyl, aryl and a cation; and $R^7$ is selected from the group consisting of amino, alkylamino, aminoalkyl, and alkylsulfanyl.

50. The pharmaceutical composition of claim 44, wherein at least one of $R^1$ or $R^2$ is acyloxy.

51. The pharmaceutical composition of claim 44, wherein at least one of $R^1$ or $R^2$ is selected from the group consisting of aliphatic and aromatic acyloxy.

52. The pharmaceutical composition of claim 50, wherein at least one of $R^1$ or $R^2$ is a hindered aliphatic acyloxy.

53. The pharmaceutical composition of claim 50, wherein said acyloxy is pivaloyloxy.

54. The pharmaceutical composition of claim 45, wherein said compound is selected from the group consisting of:

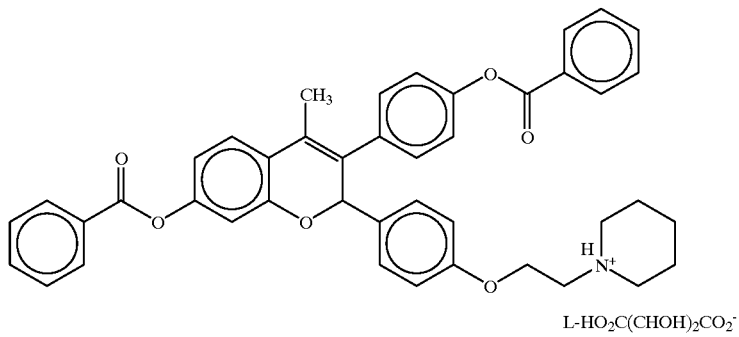
and
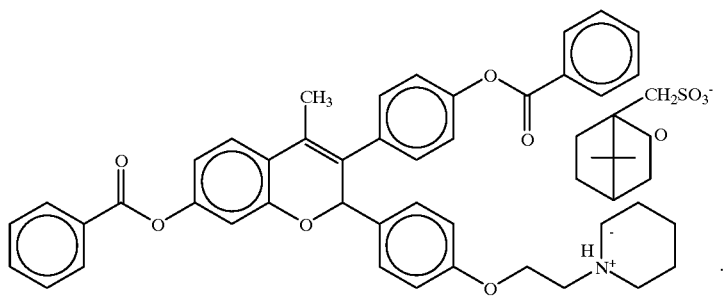
55. The pharmaceutical composition of claim 45, wherein said compound is selected from the group consisting of:
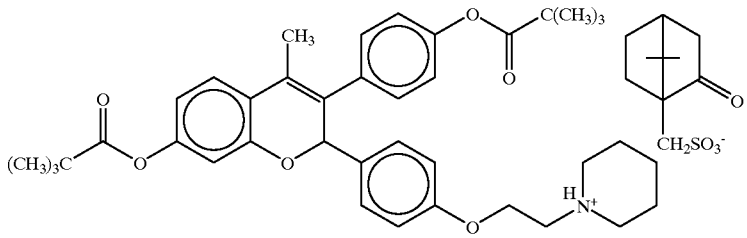
and
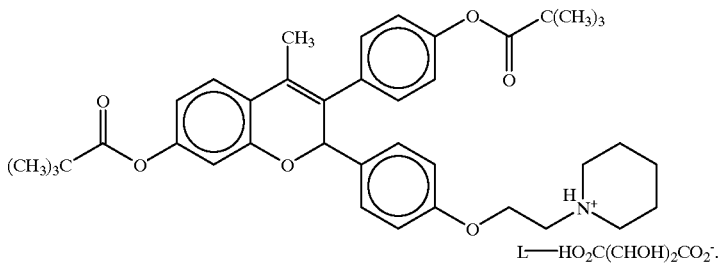
56. The pharmaceutical composition of claim 45, wherein said compound has the following molecular structure:

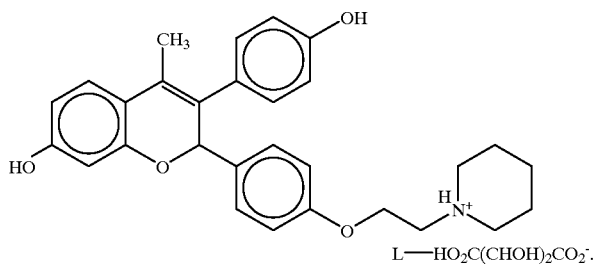

L—HO₂C(CHOH)₂CO₂⁻.

57. A pharmaceutical composition comprising a pharmaceutically acceptable diluent or carrier and a therapeutically acceptable amount of a compound or pharmaceutically effective salt thereof, having the molecular structure:

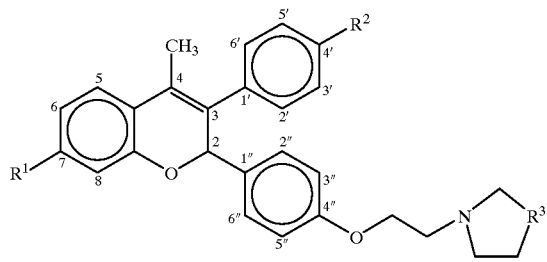

I wherein R³ is —CH₂— or —CH₂CH₂—; and wherein R¹ and R² are independently selected from the group consisting of hydroxy, acicyclic or branched aliphatic acyloxy, and $$-O-\overset{O}{\underset{\|}{C}}-R^7, \text{ and } -O-\overset{O}{\underset{\|}{C}}-OR^4$$

wherein R⁷ is selected from the group consisting of amino, alkylamino, aminoalkyl, alkylsulfanyl, alkoxy, alkenyloxy and alkynyloxy;

wherein at least one of R¹ or R² is not hydroxy.

58. The pharmaceutical composition of claim 57, wherein at least one of R¹ or R² is a alicyclic or branched aliphatic acyloxy.

59. The pharmaceutical composition of claim 57, wherein at least one of R¹ or R² is pivaloyloxy.

60. A pharmaceutical composition of claim 57, wherein said compound is selected from the group consisting of:

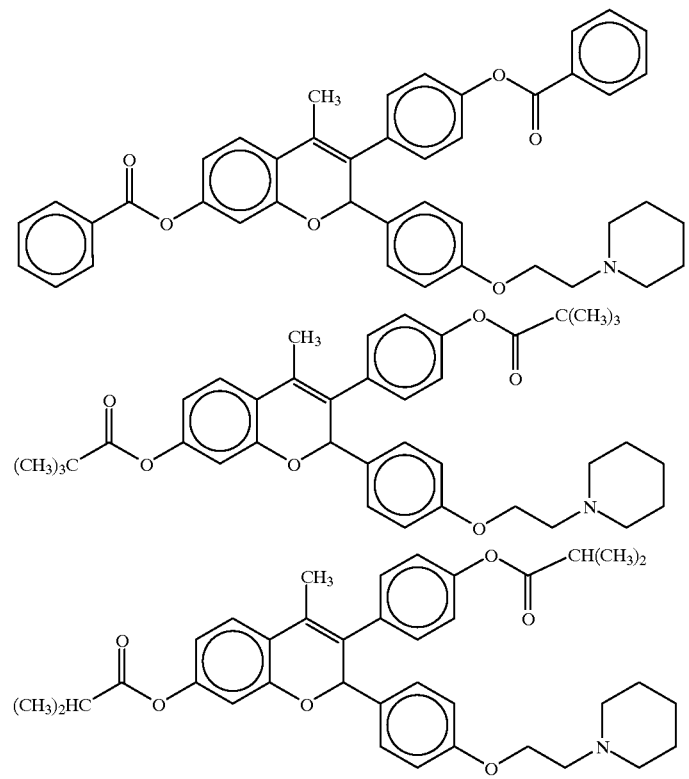

and pharmaceutically acceptable salts of any of the foregoing compounds.

61. A method of treating estrogen exacerbated diseases comprising administering to a patient in need of such treatment a therapeutically effective amount of the compound of claim 1.

62. A method of treating estrogen exacerbated diseases comprising administering to a patient in need of such treatment a therapeutically effective amount of the compound of claim 14.

63. A method of treating estrogen exacerbated diseases comprising administering to a patient in need of such treatment a therapeutically effective amount of the compound of claim 27.

64. A method of treating estrogen exacerbated diseases comprising administering to a patient in need of such treatment a therapeutically effective amount of the compound of claim 13.

65. A method of treating estrogen-exacerbated breast or endometrial cancer comprising administering to a patient in need of such treatment a therapeutically effective amount of the compound of claim 1.

66. A method of treating estrogen-exacerbated breast or endometrial cancer comprising administering to a patient in need of such treatment a therapeutically effective amount of the compound of claim 14.

67. A method of treating estrogen-exacerbated breast or endometrial cancer comprising administering to a patient in need of such treatment a therapeutically effective amount of the compound of claim 27.

68. A method of treating estrogen-exacerbated breast or endometrial cancer comprising administering to a patient in need of such treatment a therapeutically effective amount of the compound of claim 13.

69. A method of treating estrogen exacerbated diseases comprising administering to a patient in need of such treatment a therapeutically effective amount of the pharmaceutical composition of claim 31.

70. A method of treating estrogen exacerbated diseases comprising administering to a patient in need of such treatment a therapeutically effective amount of the pharmaceutical composition of claim 44.

71. A method of treating estrogen exacerbated diseases comprising administering to a patient in need of such treatment a therapeutically effective amount of the pharmaceutical composition of claim 57.

72. A method of treating estrogen exacerbated diseases comprising administering to a patient in need of such treatment a therapeutically effective amount of the pharmaceutical composition of claim 43.

73. A method of treating estrogen-exacerbated breast or endometrial cancer comprising administering to a patient in need of such treatment a therapeutically effective amount of the pharmaceutical composition of claim 31.

74. A method of treating estrogen-exacerbated breast or endometrial cancer comprising administering to a patient in need of such treatment a therapeutically effective amount of the pharmaceutical composition of claim 41.

75. A method of treating estrogen-exacerbated breast or endometrial cancer comprising administering to a patient in need of such treatment a therapeutically effective amount of the pharmaceutical composition of claim 57.

76. A method of treating estrogen-exacerbated breast or endometrial cancer comprising administering to a patient in need of such treatment a therapeutically effective amount of the pharmaceutical composition of claim 43.

77. A method of treating estrogen sensitive diseases comprising administering to a patient in need of such treatment a therapeutically effective amount of the compound of claim 10.

78. A method of treating estrogen sensitive diseases comprising administering to a patient in need of such treatment a therapeutically effective amount of the compound of claim 11.

79. A method of treating estrogen sensitive diseases comprising administering to a patient in need os such treatment a therapeutically effective amount of the pharmaceutical composition of claim 40.

80. A method of treating estrogen sensitive diseases comprising administering to a patient in need of such treatment a therapeutically effective amount of the pharmaceutical composition of claim 41.

81. A method of treating breast or endometrial cancer comprising administering to a patient in need of such treatment a therapeutically effective amount of the compound of claim 10.

82. A method of treating breast or endometrial cancer comprising administering to a patient in need of such treatment a therapeutically effective amount of the compound of claim 11.

83. A method of treating breast or endometrial cancer comprising administering to a patient in need of such treatment a therapeutically effective amount of the pharmaceutical composition of claim 40.

84. A method of treating breast or endometrial cancer comprising administering to a patient in need of such treatment a therapeutically effective amount of the pharmaceutical composition of claim 41.

\* \* \* \* \*

UNITED STATES PATENT AND TRADEMARK OFFICE
CERTIFICATE OF CORRECTION

PATENT NO. : 6,060,503
DATED : May 9, 2000
INVENTOR(S) : Fernand Labrie et al.

It is certified that error appears in the above-identified patent and that said Letters Patent is hereby corrected as shown below:

Column 2,
Line 5, change "7αa" to -- 7α --;

Column 4,
Lines 17 and 51, change "convertable" to -- convertible --;

Column 5,
Line 15, change "convertable" to -- convertible --;

Column 15,
Line 44, change "aaueous" to -- aqueous --;
Line 54, change "4dihydro-2H-pyran" to -- 4-dihydro-2H-pyran --;
Line 56, change "add" to -- acid --;

Column 17,
Line 15, change "add" to -- acid --;

Column 21,
Line 58, change "-(4'hydroxyphenyl)-" to -- -(4'-hydroxyphenyl)- --;

Column 29,
Line 16, change "benzopyran4'" to -- benzopyran-4' --
Line 55, change "4methyl" to -- 4-methyl --;
Line 56, change "7di" -- 7-di --;

Column 32,
Line 51, change "02" to -- 0.2 --;

Column 48,
Line 17, change "p-tuluenesulfonic" to -- p-toluenesulfonic --;

Column 52,
Line 16, change "acicyclic" to -- alicyclic --;

UNITED STATES PATENT AND TRADEMARK OFFICE
CERTIFICATE OF CORRECTION

PATENT NO. : 6,060,503
DATED : May 9, 2000
INVENTOR(S) : Fernand Labrie et al.

It is certified that error appears in the above-identified patent and that said Letters Patent is hereby corrected as shown below:

Column 40,
Lines 35-60, please correct the second formula therein as follows:
Change " 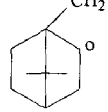 " to -- 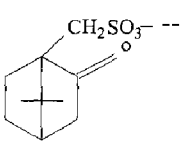 --

Column 50,
Line 21, please correct the formula therein as follows:
Change " 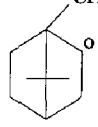 " to -- 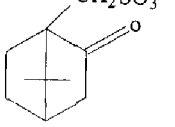 --

Signed and Sealed this

Fifth Day of April, 2005

JON W. DUDAS
*Director of the United States Patent and Trademark Office*